United States Patent
Yam et al.

(10) Patent No.: US 10,967,032 B2
(45) Date of Patent: Apr. 6, 2021

(54) OPTIMUM RATIO FOR HERBS COMBINATION OBTAINED BY USING SCIENTIFIC-BASED FORMULA FOR HYPERTENSION TREATMENT AND A COMPOSITION THEREOF

(71) Applicant: Mun Fei Yam, Pulau Pinang (MY)

(72) Inventors: Mun Fei Yam, Pulau Pinang (MY); Yean Chun Loh, Pulau Pinang (MY); Seng Hooi Loh, Pulau Pinang (MY)

(73) Assignee: Mun Fei Yam, Pulau Pinang (MY)

( * ) Notice: Subject to any disclaimer, the term of this patent is extended or adjusted under 35 U.S.C. 154(b) by 64 days.

(21) Appl. No.: 15/992,326

(22) Filed: May 30, 2018

(65) Prior Publication Data

US 2019/0060386 A1   Feb. 28, 2019

(30) Foreign Application Priority Data

Aug. 28, 2017   (MY) ............... PI 2017703167

(51) Int. Cl.
| | | |
|---|---|---|
| *A61K 36/258* | (2006.01) | |
| *A61K 36/488* | (2006.01) | |
| *A61K 36/00* | (2006.01) | |
| *A61K 36/25* | (2006.01) | |
| *A61K 36/74* | (2006.01) | |
| *A61K 36/884* | (2006.01) | |
| *A61P 9/12* | (2006.01) | |

(52) U.S. Cl.
CPC ............ *A61K 36/74* (2013.01); *A61K 36/258* (2013.01); *A61K 36/488* (2013.01); *A61K 36/884* (2013.01); *A61P 9/12* (2018.01); *A61K 2236/15* (2013.01); *A61K 2236/17* (2013.01); *A61K 2236/333* (2013.01)

(58) Field of Classification Search
None
See application file for complete search history.

(56) References Cited

FOREIGN PATENT DOCUMENTS

| CN | 104189144 A | * | 12/2014 |
| CN | 105497490 A | * | 4/2016 |
| CN | 106804826 A | * | 6/2017 |
| CN | 107029124 A | * | 8/2017 |

* cited by examiner

*Primary Examiner* — Michael Barker
*Assistant Examiner* — Randall O Winston
(74) *Attorney, Agent, or Firm* — Hamre, Schumann, Mueller & Larson, P.C.

(57) ABSTRACT

The present invention relates to a hypertension treatment. More particularly, the present invention relates to combination of four herbs' extract including 95% ethanolic extract of *U. rhynchophylla* (UR95), 95% ethanolic extract of *P. thomsonii* (PT95), 95% ethanolic extract of *P. notoginseng* (PN95), and 50% ethanolic extract of *A. orientale* (AO50) in particular range of ratio (known as F1 ratio), and all the raw herbs were then extracted in total by using 50% ethanol (known as F1-2) for use in a medicament for treating hypertension and hypertension-related complications and a composition thereof.

7 Claims, 14 Drawing Sheets

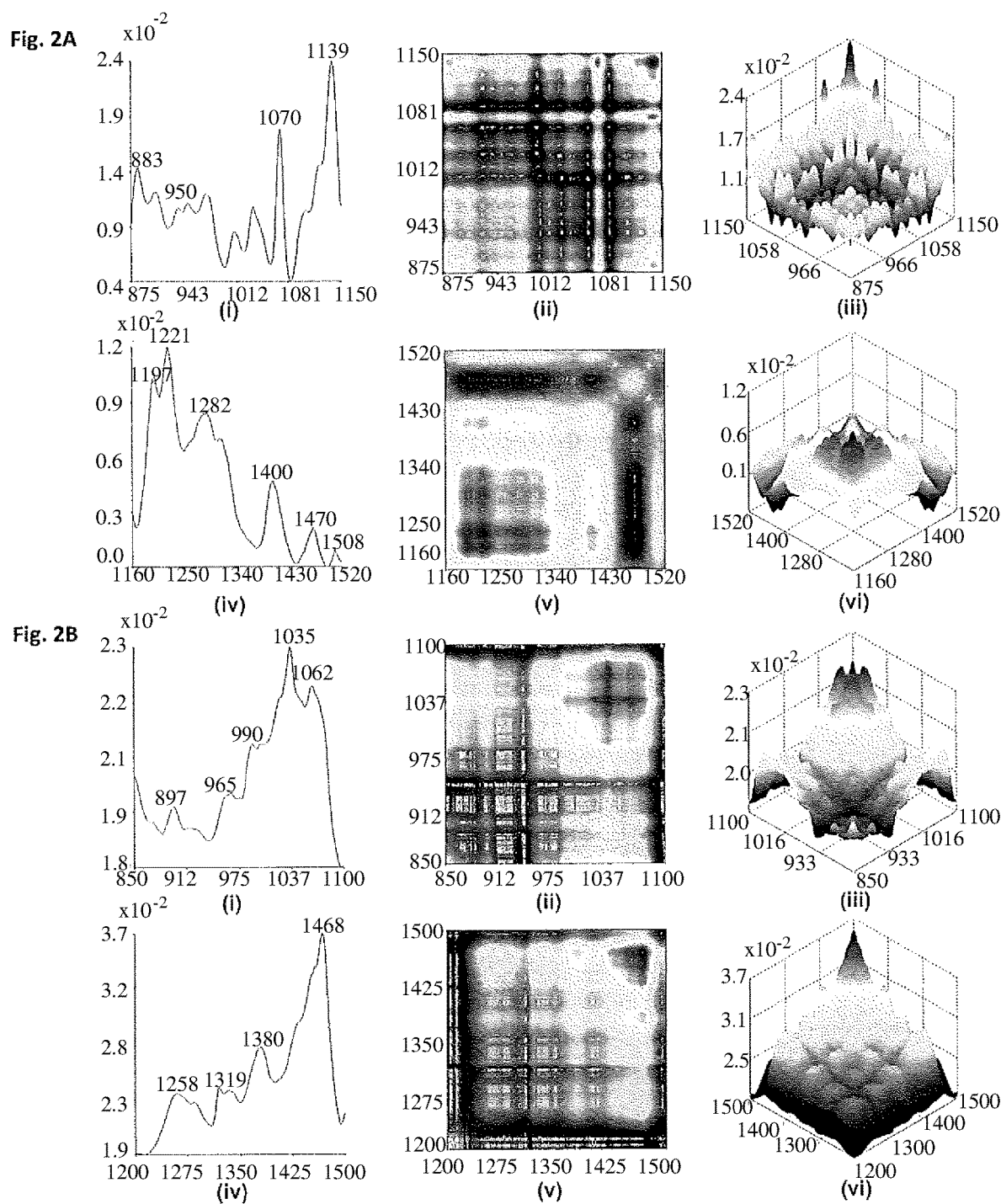

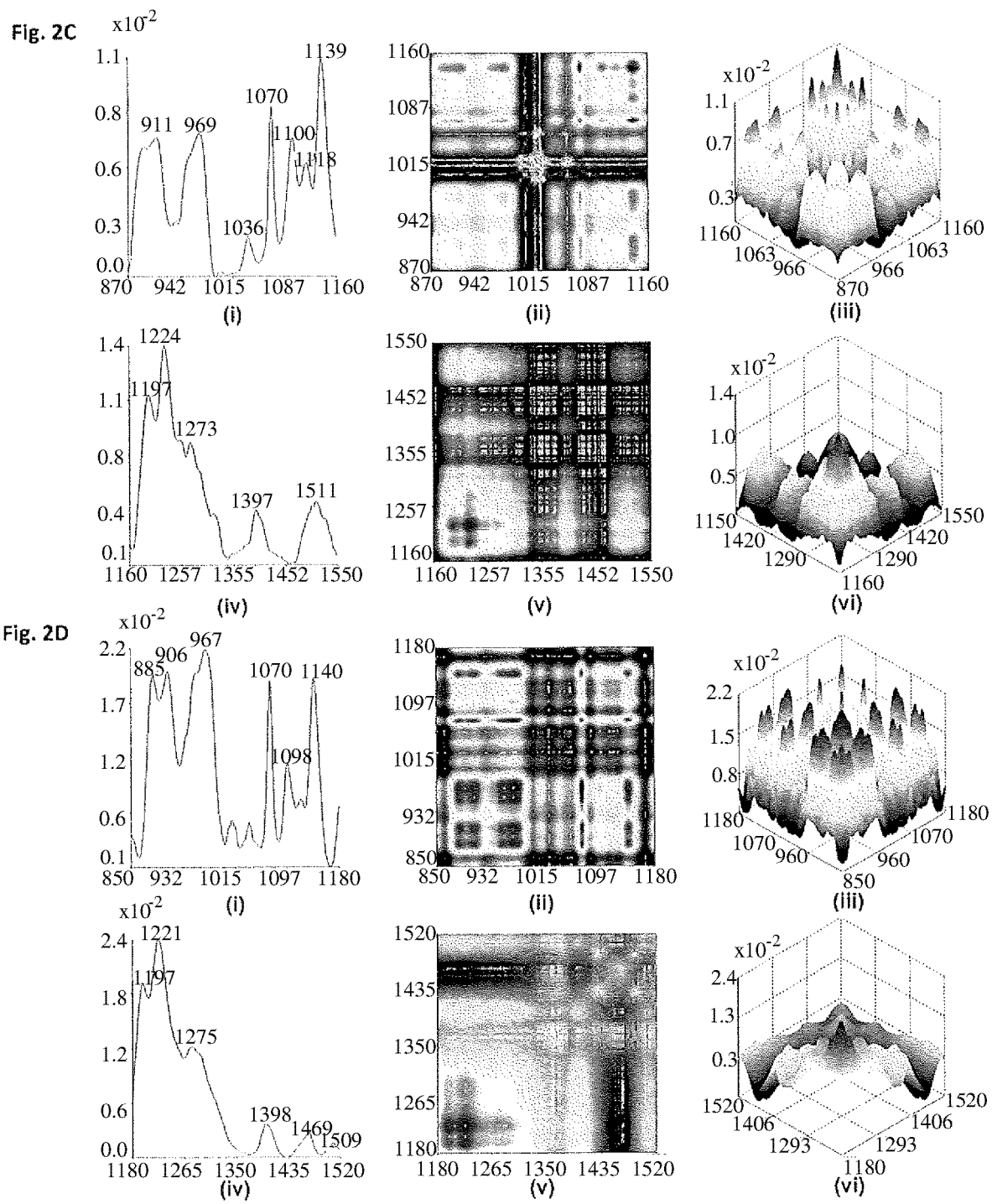

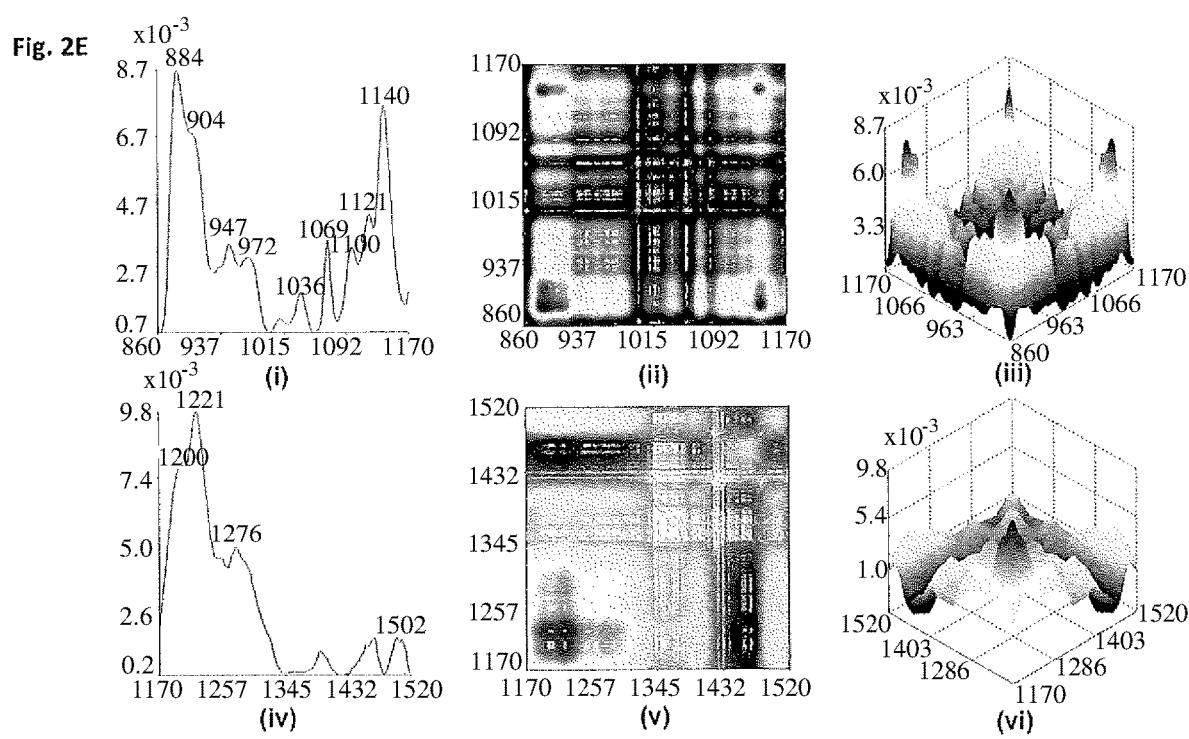

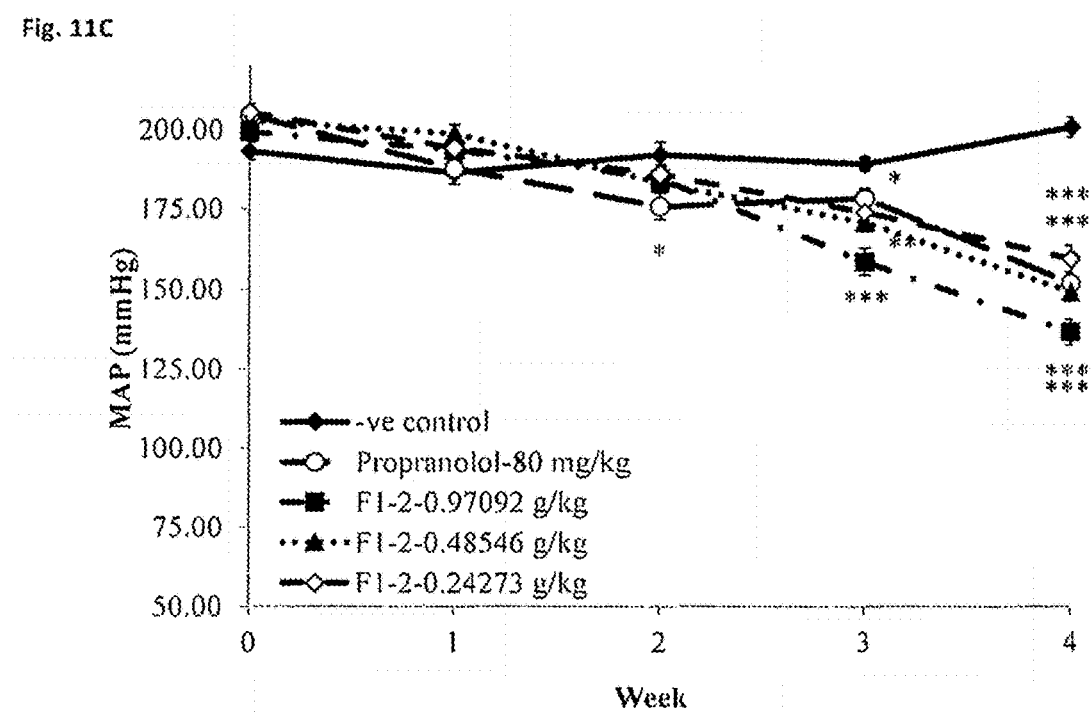

OPTIMUM RATIO FOR HERBS COMBINATION OBTAINED BY USING SCIENTIFIC-BASED FORMULA FOR HYPERTENSION TREATMENT AND A COMPOSITION THEREOF

CROSS-REFERENCE TO RELATED APPLICATION

This application claims priority from Malaysian patent application no. PI 2017703167, filed on Aug. 28, 2017.

FIELD OF THE INVENTION

The present invention relates to a hypertension treatment. More particularly, the present invention relates to combination of four herbs' extract including 95% ethanolic extract of *U. rhynchophylla* (UR95), 95% ethanolic extract of *P. thomsonii* (PT95), 95% ethanolic extract of *P. notoginseng* (PN95), and 50% ethanolic extract of *A. orientale* (AO50) in particular range of ratio (known as F1 ratio), and all the raw herbs were then extracted in total by using 50% ethanol (known as F1-2) for use in a medicament for treating hypertension and hypertension-related complications and a composition thereof.

BACKGROUND OF THE INVENTION

Hypertension is the persistently high blood pressure (BP) exerted against the walls of arteries. The force exerted by the blood is strictly dependent on the resistance of the blood vessels and the cardiac output. There were at least 32.7% of Malaysian aged 18 years old, and 43.5% of the Malaysian aged 30 years old were suffering from hypertension in 2011. Furthermore, there is approximately 1.56 billion of human worldwide are predicted to have hypertension by the year of 2025. According to American Heart Association (AHA), the ranges of the human BP can be classified as five different stages as such, normal BP is ≤120 mmHg systolic and ≤80 mmHg diastolic, pre-hypertension BP is ranged between 120-139 mmHg systolic or 80-89 mmHg diastolic, stage 1 high BP (hypertension) is 140-159 mmHg systolic or 90-99 mmHg diastolic, and stage 2 high BP (hypertension) is ≥160 mmHg systolic or ≥100 mmHg diastolic. The classification as stated by AHA is exactly the same as stated in Joint National Committee 7 (JNC 7). However, there is a critical stage of hypertension when the BP has reached ≥180 mmHg systolic or ≥110 mmHg diastolic, where the patient should be immediately treated as medical emergency. Hypertension is a silent killer, it can possess on anyone of us for years without causing any symptoms, whilst damaging our vasculatures and cardiovascular systems. In case of remaining undiagnosed, concomitant diseases including stroke, dementia, kidney diseases could be happened, and eventually causes death. Upon aging, there could be plenty of plaques building-up on the wall of the blood vessel which causing the lumen of the arteries becomes narrower, hence higher BP is required to pump the blood throughout the whole body.

There is plenty of anti-hypertensive drugs available in market. According to the clinical practice guideline in management of hypertension (4$^{th}$ edition) in Malaysia, there are five groups of antihypertensive drugs used as first line mono-therapy for newly diagnosed patient with no compelling indication which including angiotensin receptor blockers (ARBs), angiotensin-converting-enzyme inhibitors (ACEIs), thiazide-type diuretics, calcium channel blockers (CCBs), and beta blockers. However, reports showed that only around 35% of the blood pressure for hypertension patients were successfully under controlled, thus combination therapy often preferred and is necessary for those with stage 1 hypertension and above. Apparently, combination therapy is more effective then mono-therapy. At this point, we can deduce that blocking the multiple signaling mechanism pathways that causing the hypertension could be the key for treating hypertension instead of solely blocking anyone of that. Moreover, there are various chronic adverse effects reported due to the long-term consumption of anti-hypertensive drugs. For these, traditional Chinese medicine (TCM) could serve as alternative.

TCM herbs have been used to treat different kind of diseases on human since 2000 years ago. Their holistic therapeutic effects and rarely been reported to cause significant adverse effects when used in clinical have drawn the attention of scientists in latest era. There were many clinical evidences showed that the TCM physicians had treated the hypertension's patient effectively by using the TCM principles, even it is not a term in TCM. According to TCM principles, diseases will be treated according to their symptoms appeared on patient's body, while hypertension is a multi-syndromic disease that would causes "fire", phlegm-fluid retention, and deficiency syndromes. Four TCM herbs that most frequently used to treat hypertension and could counteract on its syndromes as aforementioned were selected which includes *Uncaria rhynchophylla, Pueraria thomsonii, Panax notoginseng*, and *Alisma orientale*. The most optimum ratio for four TCM herbs combination was determined by using the scientific-based formula which is orthogonal stimulus-response compatibility group studies with $L_{25}$ ($5^5$) formulation. Subsequently, the most effective solvent used to extract the combined herbs which prepared in optimum ratio was investigated as well.

CN104645091 A discloses a capsule in the treatment of hypertension, the patient can make in a short time by taking the drug after symptoms have been alleviated, with lower blood pressure and lipids easy rebound, low cost. The technical solution of the present invention is a capsule in the treatment of hypertension, characterized in that it is formulated from the following parts by weight of the drug from traditional Chinese medicine raw materials: *Astragalus* 2 parts, 20 parts of *Salvia, Pueraria* 6 parts, yam 8 parts of *Ginkgo biloba* 10 parts, 16 parts of corn, 16 parts *Gynostemma*, March 7 parts, 35 parts of hawthorn, basil 3 parts, *apocynum* 2 parts, 5 parts of wild *chrysanthemum, Prunella* 2 parts, 17 parts of *Uncaria*, medlar 16 parts, abalone 3 parts, gutta 6 parts, raw oysters 10 parts, 15 parts of white peony root, *Achyranthes* 15 parts, lotus heart 3 parts, 10 parts of *Poria, Alisma* 10 parts and 10 parts *Tianma*.

In light of the above, there appears a need for developing a medicament with fewer herb ingredients that is capable of treating hypertension and hypertension-related complications.

SUMMARY OF THE INVENTION

The present invention relates to a hypertension treatment. More particularly, the present invention relates to combination of four herbs' extract including 95% ethanolic extract of *U. rhynchophylla* (UR95), 95% ethanolic extract of *P. thomsonii* (PT95), 95% ethanolic extract of *P. notoginseng* (PN95), and 50% ethanolic extract of *A. orientale* (AO50) in particular range of ratio (known as F1 ratio), and all the raw herbs were then extracted in total by using 50% ethanol (known as F1-2) for use in a medicament for treating hypertension and hypertension-related complications and a composition thereof.

Accordingly, in one aspect of the present invention, there is provided a method for obtaining a composition for use in a medicament for treating hypertension and hypertension-related complications, characterized in that, the method comprising steps of drying *Uncaria* spp., *Pueraria* spp., *Panax notoginseng*, and *Alisma orientale*; grinding dried *Uncaria* spp., *Pueraria* spp., *Panax notoginseng*, and *Alisma orientale* into powder; mixing grounded *Uncaria* spp., *Pueraria* spp., *Panax notoginseng*, and *Alisma orientale* into a mixture wherein the grounded *Uncaria* spp., *Pueraria* spp., *Panax notoginseng*, and *Alisma orientale* is mixed in a ratio ranging from 2.32-7.35:0.44-4.44:7.24-11.24:0-3 respectively; subjecting the mixture to an extraction method selected from a group comprising maceration, liquid-liquid extraction, decoction, solid-phase extraction, solid-phase microextraction, Soxhlet extraction, and fizzy extraction; and separating an extract containing the composition from the mixture.

In a preferred embodiment, the ratio of the grounded *Uncaria* spp. to *Pueraria* spp. to *Panax notoginseng* to *Alisma orientale* is 5.32:2.44:9.24:1 respectively.

In another aspect of the present invention, there is provided a composition for use in a medicament for treating hypertension and hypertension-related complications obtainable by a method, characterized in that, the method comprising steps of drying *Uncaria* spp., *Pueraria* spp., *Panax notoginseng*, and *Alisma orientale*; grinding dried *Uncaria* Spp., *Pueraria* spp., *Panax notoginseng*, and *Alisma orientale* into powder; mixing grounded *Uncaria* spp., *Pueraria* spp., *Panax notoginseng*, and *Alisma orientale* into a mixture wherein the grounded *Uncaria* spp., *Pueraria* spp., *Panax notoginseng*, and *Alisma orientale* is mixed in a ratio ranging from 2.32-7.35:0.44-4.44:7.24-11.24:0-3 respectively; subjecting the mixture to an extraction method selected from a group comprising maceration, liquid-liquid extraction, decoction, solid-phase extraction, solid-phase microextraction, Soxhlet extraction, and fizzy extraction; and separating an extract containing the composition from the mixture.

In the last aspect of the present invention, there is provided a use of the composition according to the second aspect of the present invention in the manufacture of a medicament for hypertension and hypertension-related complications.

It is an object of the present invention to provide a novel approach for treating hypertension by producing a composition that can induce up to 101.71±3.64% of maximum relaxation ($R_{max}$) value in the phenylephrine (PE)-primed pre-contracted rat aortic rings at final concentration of 0.3175 mg/ml, with $EC_{50}$ value of 0.028±0.005 mg/ml.

It is another object of the present invention to provide a novel approach for treating hypertension by producing a composition that can exhibit antihypertensive effect on spontaneous hypertensive rats (SHRs) in vivo with systolic BP reduced to 168.69±3.59 mmHg from 225.81±2.77 mmHg compared to control, diastolic BP reduced to 121.86±4.58 mmHg from 189.19±3.61 mmHg compared to control, and MAP reduced to 136.78±4.07 mmHg from 200.97±3.22 mmHg compared to control after 28 days of sub-chronic oral administration of 0.97092 g/kg of F1-2.

It is yet another object of the present invention to provide a novel approach for treating hypertension by producing a composition that can exhibit vasodilatory effect by employing NO/sGC/cGMP, $PGI_2$, muscarinic-receptor and beta-adrenergic receptors pathways.

It is also an object of the present invention to provide a novel approach for treating hypertension by producing a composition that can regulate vascular tone by controlling membrane potential of vascular smooth muscle cell via calcium activated ($K_{ca}$), voltage-operated ($K_v$), ATP-sensitive ($K_{ATP}$), and inwardly-rectifying ($K_{ir}$) potassium channels. By acting as the potassium channels opener, the composition can enhance the hyperpolarizing current by allowing the potassium efflux from the cytosol.

It is yet another object of the present invention to provide a novel approach for treating hypertension by producing a composition that can act as calcium channels blocker for both voltage-operated calcium channels (VOCC) and inositol triphosphate receptor ($IP_3R$) to decrease the depolarizing current in vascular smooth muscle cells by inhibiting the calcium influx into the cytosol, hence reduce the formation of calcium-calmodulin complexes, and therefore causing vasodilatory effects.

The present invention consists of certain novel features and a combination of parts hereinafter fully described and illustrated in the accompanying drawings and particularly pointed out in the appended claims; it being understood that various changes in the details may be without departing from the scope of the invention or sacrificing any of the advantages of the present invention.

BRIEF DESCRIPTION OF THE DRAWINGS

For the purpose of facilitating an understanding of the invention, there is illustrated in the accompanying drawings the preferred embodiments from an inspection of which when considered in connection with the following description, the invention, its construction and operation and many of its advantages would be readily understood and appreciated.

FIG. 2A is a series of graphs illustrating the autopeak curves (i), 2D-IR (ii), and 3D-IR (iii) in the range of 1150-875 $cm^{-1}$ and autopeak curves (iv), 2D-IR (v), and 3D-IR (vi) in the range of 1520-1160 $cm^{-1}$ for *G. elata* according to an example of the present invention.

FIG. 2B is a series of graphs illustrating the autopeak curves (i), 2D-IR (ii), and 3D-IR (iii) in the range of 1100-850 $cm^{-1}$ and the autopeak curves (iv), 2D-IR (v), and 3D-IR (vi) in the range of 1500-1200 $cm^{-1}$ for *U. rhynchophylla* according to an example of the present invention.

FIG. 2C is a series of graphs illustrating the autopeak curves (i), 2D-IR (ii), and 3D-IR (iii) in the range of 1160-870 $cm^{-1}$ and autopeak curves (iv), 2D-IR (v), and 3D-IR (vi) in the range of 1550-1160 $cm^{-1}$ for *P. thomsonii* according to an example of the present invention.

FIG. 2D is a series graphs illustrating the autopeak curves (i), 2D-IR (ii), and 3D-IR (iii) in the range of 1180-850 $cm^{-1}$ and autopeak curves (iv), 2D-IR (v), and 3D-IR (vi) in the range of 1520-1180 cm$^{-1}$ for *P. notoginseng* according to an example of the present invention.

FIG. 2E is a series of graphs illustrating the autopeak curves (i), 2D-IR (ii), and 3D-IR (iii) in the range of 1170-860 cm$^{-1}$ and autopeak curves (iv), 2D-IR (v), and 3D-IR (vi) in the range of 1520-1170 cm$^{-1}$ for *A. orientale* according to an example of the present invention.

FIG. 11C is a graph illustrating the antihypertensive effect of 0.97092 g/kg (high dose), 0.48546 g/kg (medium dose), and 0.24273 g/kg (small dose) of F1-2, and 80 mg/kg propranolol (positive control) on mean arterial pressure (MAP) of SHRs during 28 days of oral administration and compared to the control group (*: $P<0.05$; : $P<0.01$; *: $P<0.001$; Mean±S.E.M.; n=6).

DETAILED DESCRIPTION OF THE INVENTION

Figure 1A:
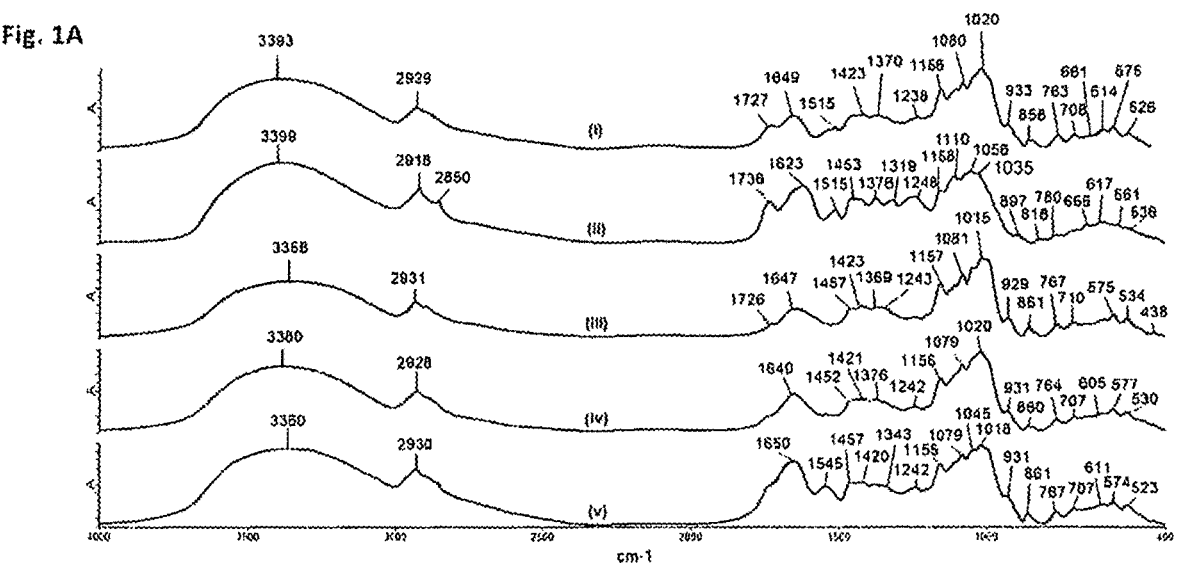
FIG. 1A is a graph illustrating a one-dimensional infrared spectra in the ranges of 4000 to 400 $cm^{-1}$ for raw herbs powders *Gastrodia elata* (i), *Uncaria rhynchophylla* (ii), *Pueraria thomsonii* (iii), *Panax notoginseng* (iv), and *Alisma orientale* (v) according to an example of the present invention.

The present invention relates to a hypertension treatment. More particularly, the present invention relates to combination of four herbs' extract including 95% ethanolic extract of *U. rhynchophylla* (UR95), 95% ethanolic extract of *P. thomsonii* (PT95), 95% ethanolic extract of *P. notoginseng* (PN95), and 50% ethanolic extract of *A. orientale* (AO50) in particular range of ratio (known as F1 ratio), and all the raw herbs were then extracted in total by using 50% ethanol (known as F1-2) for use in a medicament for treating hypertension and hypertension-related complications and a composition thereof. Hereinafter, the method and the composition by said method shall be described according to the preferred embodiments of the present invention and by referring to the accompanying description and drawings. However, it is to be understood that limiting the description to the preferred embodiments of the invention and to the drawings is merely to facilitate discussion of the present invention and it is envisioned that those skilled in the art may devise various modifications without departing from the scope of the appended claim.

*Uncaria* is a genus of flowering plants in the family of Rubiaceae. It has about 40 species. Their distribution is pantropical, with most species native to tropical Asia, three from Africa and the Mediterranean and two from the neotropics. They are known colloquially as gambier, cat's claw or uña de gato. Among the species of the *Uncaria* genus that may be used in the method of producing a composition for treating hypertension according to an embodiment of the present invention are, but not limited to, *Uncaria rhynchophylla* (Miq.) Jacks, *Uncaria macrophylla* Wall, *Uncaria hirsute* Havil, *Uncaria sinensis* (Oliv.) Havil and *Uncaria sessilifructus* Roxb and any mentioned species in Chinese Pharmacopeia related to the medicinal plant "gou teng". *U. rhynchophylla* or *Uncaria rhynchophylla* is categorized as herb that can soothe the liver, and extinguish wind. It commonly used to calm the liver, extinguish vertigo and spasms, clear heat and lower blood pressure (BP).

*Pueraria* is a genus of 15-20 species of plants native to Asia. *Pueraria* flower is used in traditional Chinese medicine to reduce reactions to alcohol consumption. Among the species of the *Pueraria* genus that may be used in the method of producing a composition for treating hypertension according to an embodiment of the present invention are, but not limited to *Pueraria lobata* and *Pueraria thomsonii*. *Pueraria thomsonii* or *P. thomsonii* has been used in traditional Chinese medicine for treatment of fever, acute dysentery, diarrhea, diabetes, and cardiovascular diseases. *P. thomsonii* is a cool-acrid herb that capable to release the exterior. It often used to promote fluid production to quench thirst, arrest warmed-body, and release flesh.

*Panax notoginseng* or *P. notoginseng* was claimed as most valuable medicinal herb that categorized as herb that help to stop bleeding, invigorate blood, staunch bleeding, relieve pain, and effective to be used for trauma treatment. *Panax notoginseng* is a species of the genus *Panax*, and it is most commonly referred to in English as *notoginseng*. In Chinese it is called *tienchi ginseng* or *sanchi*, three-seven root, and mountain plant. *P. notoginseng* belongs to the same scientific genus as Asian *ginseng*. In Latin, the word *panax* means "cure-all", and the family of *ginseng* plants is one of the best-known herbs. *P. notoginseng* grows naturally in China and Japan. The herb is a perennial with dark green leaves branching from a stem with a red cluster of berries in the middle. It is both cultivated and gathered from wild forests, with wild plants being the most valuable. The Chinese refer to it as three-seven root because the plant has three petioles with seven leaflets each. It is also said that the root should be harvested between three and seven years after planting it. *P. notoginseng* contains dammarane-type ginsenosides as major constituents. Dammarane-type ginsenosides includes 2 classifications: the 20(S)-protopanaxadiol (ppd) and 20(S)-protopanaxatriol (ppt) classifications. *P. notoginseng* contains high levels of Rb1, Rd (ppd classification) and Rg1 (ppt classification) ginsenosides. Rb1, Rd and Rg1 content of *P. notoginseng* is found to be higher than that of *P. ginseng* and *P. quinquefolius* in one study.

*Alisma orientale* or *A. orientale* is a famous diuretic agent that helps to remove dampness, drain water, increase urination, relieve vertigo, and decrease the blood lipid. *Alisma orientale* is sometimes treated as a variety of *Alisma plantago-aquatica* (*Alisma plantago-aquatica* var. *orientale*). The plant grows to about 1 m tall. It is in flower from June to August, and the seeds ripen from July to September. The flowers are hermaphrodite (have both male and female organs) and are pollinated by flies. The plant cannot grow in the shade. It requires wet soil and can grow in water. The rhizomes of *A. orientale* have been used as a traditional Chinese medicine, ze xie. The rhizome of the plant is also an herb used in kampo Japanese medicine. The seed contains cis-aconitic anhydride ethyl ester and cis-2,4,5-trihydroxycinnamic acid.

Accordingly, in one aspect of the present invention, there is provided a method for obtaining a composition for use in a medicament for treating hypertension and hypertension-related complications, characterized in that, the method comprising steps of drying *Uncaria* spp., *Pueraria* spp., *Panax notoginseng*, and *Alisma orientale*; grinding dried *Uncaria* spp., *Pueraria* spp., *Panax notoginseng*, and *Alisma orientale* into powder; mixing grounded *Uncaria* spp., *Pueraria* spp., *Panax notoginseng*, and *Alisma orientale* into a mixture wherein the grounded *Uncaria* spp., *Pueraria* spp., *Panax notoginseng*, and *Alisma orientale* is mixed in a ratio ranging from 2.32-7.35:0.44-4.44:7.24-11.24:0-3 respectively; subjecting the mixture to an extraction method selected from a group comprising maceration, liquid-liquid extraction, decoction, solid-phase extraction, solid-phase microextraction, Soxhlet extraction, and fizzy extraction; and separating an extract containing the composition from the mixture.

In a preferred embodiment, *Uncaria* Spp., *Pueraria* spp., *Panax notoginseng*, and *Alisma orientale* are prepared in effective concentration of $EC_{15-35}$, $EC_{10-30}$, $EC_{10-30}$, and $EC_{1-20}$, respectively. The ratio of the grounded *Uncaria* spp. to *Pueraria* spp. to *Panax notoginseng* to *Alisma orientale* is 5.32:2.44:9.24:1 respectively. It is preferred that *Uncaria* Spp is selected from, but not limited to, a group comprising *Uncaria rhynchophylla* (Miq.) Jacks, *Uncaria macrophylla* Wall, *Uncaria hirsute* Havil, *Uncaria sinensis* (Oliv.) Havil and *Uncaria sessilifructus* Roxb. It is preferred that *Pueraria* spp. is selected from, but not limited to, a group comprising *Pueraria thomsonii*, *Pueraria lobata*, *Pueraria edulis*, *Pueraria montana*, *Pueraria phaseoloides*, *Pueraria bella*, *Pueraria mirifica*, *Pueraria omeiensis*, *Pueraria peduncularis*, *Pueraria tuberosa* and *Pueraria wallichii*.

It is preferred that the maceration utilized an extraction solvent selected from a group comprising, but not limited to, ethanol, water, hexane, ethyl acetate, chloroform, acetone or other chemical solvents. In an embodiment, it is preferred that the concentration of ethanol is 50% ethanol.

The extracts are separated from its solvent at a temperature preferably 50° C. for a period of preferably 48 hours through a method selected from a group comprising, but not limited to, freeze-drying, rotary-evaporation and spray-drying.

In another aspect of the present invention, there is provided a composition for use in a medicament for treating hypertension and hypertension-related complications obtainable by a method, characterized in that, the method comprising steps of drying *Uncaria* spp., *Pueraria* spp., *Panax notoginseng*, and *Alisma orientale*; grinding dried *Uncaria* spp., *Pueraria* spp., *Panax notoginseng*, and *Alisma orientale* into powder; mixing grounded *Uncaria* spp., *Pueraria* spp., *Panax notoginseng*, and *Alisma orientale* into a mixture wherein the grounded *Uncaria* spp., *Pueraria* spp., *Panax notoginseng*, and *Alisma orientale* is mixed in a ratio ranging from 2.32-7.35:0.44-4.44:7.24-

11.24:0-3 respectively; subjecting the mixture to an extraction method selected from a group comprising maceration, liquid-liquid extraction, decoction, solid-phase extraction, solid-phase microextraction, Soxhlet extraction, and fizzy extraction and separating an extract containing the composition from the mixture.

It is preferred that the composition does not comprise any other herbs except from *Uncaria* spp., *Pueraria* spp., *Panax notoginseng*, and *Alisma orientale*, additive, enhancer, colouring, flavouring, and stabiliser in any mixture ratio nor sequence with potential alteration to hypertension related treatment effect.

In the third and last aspect of the present invention, there is provided a use of the composition according to the second aspect of the present invention in the manufacture of a medicament for hypertension and hypertension-related complications.

The method of producing a composition for use in treating hypertension as described above has many advantages. The composition, produced through the method, can induce up to 101.71±3.64% of maximum relaxation ($R_{max}$) value in the phenylephrine (PE)-primed pre-contracted aortic rings at final concentration of 0.3175 mg/ml, with $EC_{50}$ value of 0.028±0.005 mg/ml. The composition can exhibit vasodilatory effect by employing NO/sGC/cGMP, $PGI_2$, muscarinic-receptor and beta-adrenergic receptors pathways. The composition can also regulate vascular tone by controlling membrane potential of vascular smooth muscle cell via calcium-activated ($K_{ca}$), voltage-operated ($K_v$), ATP-sensitive ($K_{ATP}$), and inwardly-rectifying ($K_{ir}$) potassium channels. By acting as the potassium channels opener, the composition can enhance the hyperpolarizing current by allowing the potassium efflux from the cytosol. Besides that, the composition can act as calcium channels blocker for both voltage-operated calcium channels (VOCC) and inositol triphosphate receptor ($IP_3R$) to decrease the depolarizing current in vascular smooth muscle cells by inhibiting the calcium influx into the cytosol, hence reduce the formation of calcium-calmodulin complexes, and therefore causing vasodilatory effects. In in vivo test, F1-2 can exhibit antihypertensive effect on spontaneous hypertensive rats (SHRs) in vivo with systolic BP reduced to 168.69±3.59 mmHg from 225.81±2.77 mmHg compared to control, diastolic BP reduced to 121.86±4.58 mmHg from 189.19±3.61 mmHg compared to control, and MAP reduced to 136.78±4.07 mmHg from 200.97±3.22 mmHg compared to control after 28 days of sub-chronic oral administration of 0.97092 g/kg of F1-2.

The present invention will now be described in further detail by way of examples.

EXAMPLE 1

Vasodilatory Effects of Combined Traditional Chinese Medicinal (TCM) Herbs in Optimized Ratio In this example, five TCM herbs that were most frequently used in clinical prescriptions to counteract different obligate syndromes of hypertension were chosen to achieve antihypertensive effects with higher efficacies. *Gastrodia elata* and *Uncaria rhynchophylla* belong to the category of herbs that calm the liver and extinguish "wind" based on TCM principles. *G. elata* is known to extinguish "wind", arrest spasms, relieve vertigo with pain, and soothe the channels and collaterals. *U. rhynchophylla* is known to clear heat, calm the liver, decrease blood pressure, and extinguish vertigo and spasms. *Pueraria thomsonii* is categorized as a cool-acrid herb that releases the exterior. It is best in releasing flesh, arresting fever, promoting fluid production to quench thirst, and relieving neck rigidity. *Panax notoginseng* is categorized as an herb that stops bleeding and specializes in staunching bleeding, invigorating blood, and relieving pain. It is famous for its use in trauma treatment and *Alisma orientale* is a well-known diuretic agent belonging to the category of herbs that drain water and dampness, promote urination, lower blood lipid, and relieve vertigo. Studies of its vasodilatory effects have utilized isolated rat aortic ring experiments, as it is well known as the "golden tool" for antihypertensive drug development due to its high reliability. Thus, the isolated rat aortic ring model was chosen for this example. It aimed to discover the best combination ratio of five TCM herbs for efficacy in treating hypertension.

Materials and Methods

Plants and Chemicals

The *G. elata, U. rhynchophylla, P. thomsonii, P. notoginseng*, and *A. orientale* herbs were purchased from the local medical hall. Acetylcholine (Ach) and phenylephrine (PE) were bought from Acros Organics (Belgium). Both chemicals were dissolved in distilled water before use. The herbal extracts were dissolved in distilled water at a concentration of 128 mg/ml to form as stock and stored in freezer at −20° C.

Tri-Step FTIR Characterization

The five herbs wore ground into powder and passed through a 200-mesh sieve to obtain fine powder prior to the tri-step Fourier transform infrared (FTIR) spectroscopic analysis. A tablet of potassium bromide (KBr) was used as the blank. About 1 mg of herb powder was mixed with 100 mg of KBr and compressed into a small thin tablet by applying a pressure of approximately 10 psi. The spectra of five herbs were recorded at an optical path speed of 0.2 cm/s with 16 co-added scans in a resolution of 4 $cm^{-1}$ between wavelengths of 4000-400 $cm^{-1}$ using the Spectrum 400 FTIR spectrometer (v 6.3.5) equipped with a DTGS detector (Perkin-Elmer, USA). The disturbances caused by carbon dioxide and water were directly removed online while scanning. The results were considered valid when transmission of 60% or more was achieved, or else the test has to be repeated by adding either more sample or KBr.

The second derivative IR (SD-IR) was performed by using the Savitzky-Golay polynomial fitting (13-point smoothing). The two-dimensional IR (2D-IR) spectra were obtained by placing the sample tablet into the sample holder with a programmable heated jacket controller (Model GS20730, Specac). The dynamic spectra were recorded at temperatures ranging from 50-120° C. at intervals of 10° C. The 2D-IR correlation spectra were obtained by treating the series of dynamic spectra with 2D-IR correlation analysis software developed by Tsinghua University (Beijing, China).

Preparation of Herb Extracts

The *G. elata, U. rhynchophylla, P. thomsonii, P. notoginseng*, and *A. orientale* herbs were cut into smaller pieces and dried in the oven at 50° C. for 3 days until a constant weight was achieved. The herbs were ground into fine powder by using mill. Approximately 200 g of herb powder was prepared in three different containers, and each herb was soaked with 95% ethanol, 50% ethanol, or distilled water, individually. The five powdered herbs macerated with 95% ethanol were labelled as GE95, UR95, PT95, PN95, and AO95. Those macerated with 50% ethanol were labelled as GE50, UR50, PT50, PN50, and AO50, whereas those macerated with distilled water were labelled as GEW, URW, PTW, PNW, and AOW. The maceration process was executed at a temperature of 50° C. for 48 h and repeated three times. They were then filtered. The filtrate obtained was concentrated by using rotary evaporator at 50° C. under reduced pressure. The concentrated filtrates were known as herbal extracts. All the extracts were freeze-dried and kept in desiccators at 4° C. for future use.

Animals

The male Sprague Dawley (SD) rats aging between eight to ten weeks old with the weight between 180-250 g were obtained from the Universiti Sains Malaysia (USM) Animal Research and Service Centre (ARASC). The SD rats were transited into the animal transit room with the ambient temperature of 27° C. with 12-hour light/dark cycle, and allowed free access to food and water. All the animal involved experiments studies were performed under the surveillance of the Guideline in Care and Use of Laboratory Animal by Universiti Sains Malaysia with the approved protocol in advance, USM/Animal Ethics Approval/2016/(103) (770, 774-777).

Preparation of Rat Aortic Rings and In Vitro Assays

Before the aortic rings preparation, the Krebs-Henseleit (Krebs') solution (118.0 mM NaCl, 4.7 mM KCl, 25.0 mM $NaHCO_3$, 2.5 mM $CaCl_2$, 1.2 mM $KH_2PO_4$, 1.2 mM $MgSO_4$, and 11.0 mM glucose, pH 7.4) was prepared in a Petri dish and aerated with carbogen (5% of $CO_2$ and 95% of $O_2$) at 37° C. A male SD rat was sacrificed by overdose inhalation of $CO_2$ for around 2 minutes. Then, the aorta (segment near to the heart was preferred) of the rat was isolated from the body immediately and placed in Krebs' solution. The isolated aorta was cleaned by discarding the adhered adipose tissue, and was trimmed into 3-4 mm long of aortic ring segments. Subsequently, the aortic rings were mounted in the Krebs' solution (10 ml) containing tissue bath by using two needle hooks with temperature maintained at 37° C. and continuously aerated with carbogen gas. One hook was fixed on L-shaped braces and another hook was connected to the force-electricity transducer (GRASS Force-Displacement Transducer FT03 C Isometric Measurement). The mounted aortic rings were allowed to equilibrate for at least 45 minutes with Krebs' solution changed at every 15 minutes interval. The resting tension was re-adjusted to 1.0 g when necessary. Once the tension of the mounted aortic rings was stabilized, the contractile agent, PE (1 µM), and relaxing agent, Ach (1 µM) were added accordingly, the validity of the aortic rings was assured with at least 60% of responses achieved. After that, the aortic rings were rinsed with Krebs' solution for three times at 15 minutes interval. The resting tension was re-adjusted to 1.0 g only when necessary before PE (1 µM) pre-contraction.

Vascular Response to Herbs' Extracts on PE Pre-Contracted Aortic Rings

When the PE-induced contraction on the endothelium-intact isolated aortic rings has reached a plateau, the herb' extract (100 µl) was added cumulatively into the tissue bath (0.25-128 mg/ml which equal to final concentration of 2.5575 mg/ml in the tissue bath) at 20 minutes interval. The vascular response was detected by force-electricity transducer, and amplified by Quad Bridge amp (AD instrument Australia), which was subsequently converted into digital signals by powerLab 26T (AD instrument, Australia). The cumulative concentration-response curve of each herb's extract was constructed. The $EC_{10}$, $EC_{15}$, $EC_{20}$, and $EC_{25}$ of UR95, PT95, PN95, and AO50 were calculated from their respective concentration-response curves and used for orthogonal stimulus-response compatibility group studies.

Orthogonal Stimulus-Response Compatibility Group Studies

The orthogonal stimulus-response compatibility group screening was arranged by using $L_{25}$ ($5^5$) formula and forming 25 sets of experiments at which their ratios would not be repeated in other sets of experiments. Their expected relaxation (ER) values, corresponding to each set of the experiments, should not exceed 100% so that the resulting actual relaxation (AR) is valid. The efficacy of each set of the experiments was calculated as (AR/ER)×100%. The formula that exhibited the highest efficacy would be assumed to be the most optimum ratio (F1). The comparison studies of the calculated optimum ratio (calculated from orthogonal stimulus-response compatibility table), experimental optimum ratio, and formulae that exhibited a vasodilatory effect close to the experimental optimum ratio were carried out to confirm the potential of F1 in terms of vasodilatory effect.

Efficacy of Extracts Using Different Extraction Methods Following the F1 Ratio

After the formulation of F1, the vasodilatory effects of the extracts prepared by using different extraction solvents and extraction methods of the five herbs following the ratio of F1 were investigated. The powders of five raw herbs were prepared in exactly the same ratio as F1 and total extraction at 50° C. was conducted using distilled water, 50% ethanol, and 95% ethanol, separately. The extracts were labelled as F1-1, F1-2, and F1-3, respectively. Second, U. rhynchophylla, P. thomsonii, and P. notoginseng were prepared following the ratio as in F1, extracted at 50° C. using 95% ethanol, subsequently mixed with the 50% ethanolic extract of A. orientale (following the ratio of F1), and labelled as F1-4. Finally, a total extraction of the five herbs following the ratio of F1 was performed by using distilled water at 100° C. and labelled as F1-5. The vasodilatory effects wore determined by using the in vitro isolated rat aortic ring model. The concentration-response curves were compared among F1 and other F1 derivative groups.

Statistical Analysis

All data are expressed as mean±SEM. Statistical analysis was performed using one-way analysis of variance using SPSS version 22 software. All tests were two-tailed and the significance was set at P<0.05.

Results

Tri-Step FTIR Macro-Fingerprint Analysis

Figure 1B:
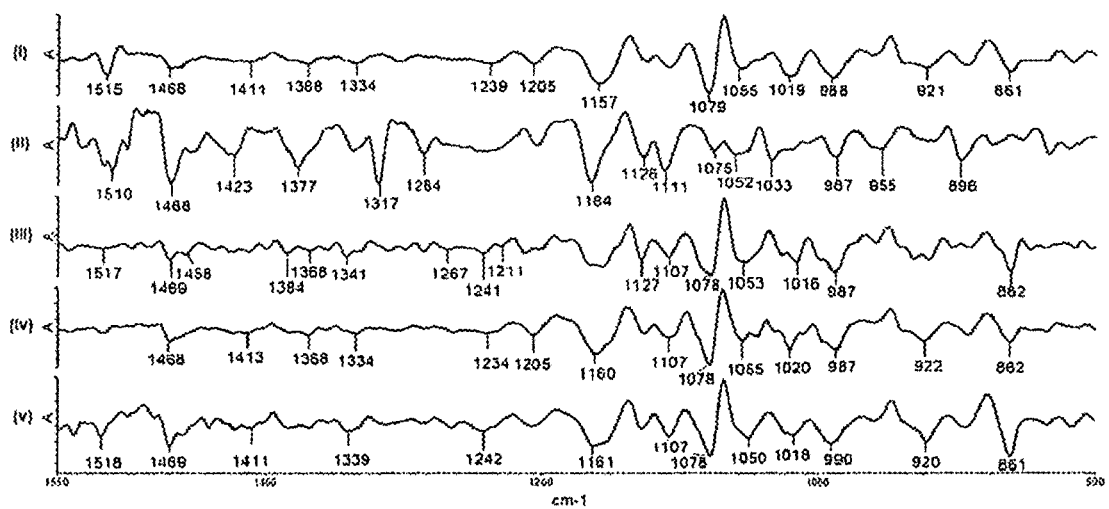
FIG. 1B is a graph illustrating a second-derivative infrared spectra in the ranges of 1550 to 800 $cm^{-1}$ for raw herbs powders *Gastrodia elata* (i), *Uncaria rhynchophylla* (ii), *Pueraria thomsonii* (iii), *Panax notoginseng* (iv), and *Alisma orientale* (v) according to an example of the present invention.

Tri-step FTIR spectroscopic analysis was performed to identify the fingerprints of G. elata, U. rhynchophylla, P. thomsonii, P. notoginseng, and A. orientale. Their 1D-IR, SD-IR, and 2D-IR spectra were compared with the atlas of Sun et al., (2003) to verify the authenticity of these five herbs. The main components and the holistic variations of the chemical constituents were also reported. As shown in FIG. 1A, the conventional FTIR spectra of all the five herbs are identical to the spectra in the atlas of TCM published by Sun et al., (2003), which proved the authenticity of these herbs. To further distinguish the differences between the peaks characteristics, SD-IR spectroscopy was performed and the spectra within the range of 1550-850 $cm^{-1}$ were shown in FIG. 1B. It can be seen that among the herbs, the SD-IR spectrum of U. rhynchophylla was the most unique in terms of peak intensity rather than peak position, which indicated the possibility of a higher content of vasoactive constituents. In addition, the relationship between the chemical constituents in each herb could be determined by applying external perturbation. For instance, different temperatures were applied to the 2D-IR spectroscopic analysis of these herbs and the resulting dynamic spectra of G. elata, U. rhynchophylla, P. thomsonii, P. notoginseng, and A. orientale were shown in FIGS. 2A, 2B, 2C, 2D, and 2E, respectively. The dynamic spectra obtained were completely different from one another, which facilitated the identification among different herbs and their chemical structures.

Figure 3A:
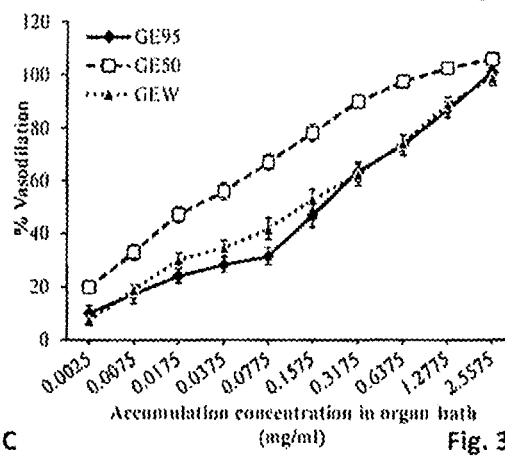
FIG. 3A is a graph illustrating the vasodilatory effect of 95% ethanolic (GE95), 50% ethanolic (GE50), and distilled water (GEW) extracts of *G. elata* with cumulative concentration of 0.0025-2.5575 mg/ml on 1 µM PE pre-contracted isolated endothelium-intact Sprague Dawley (SD) rat aortic rings (n=8) according to an example of the present invention.
Figure 3B:
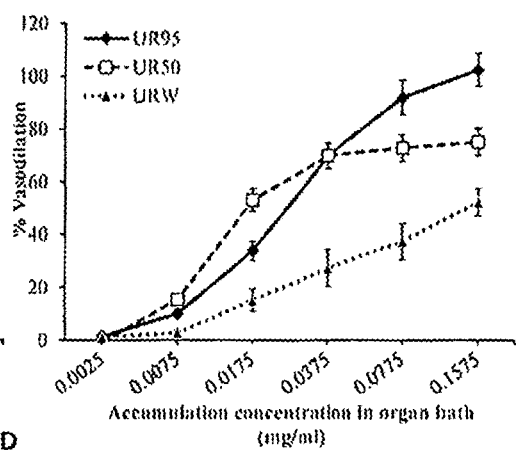
FIG. 3B is a graph illustrating the vasodilatory effect of 95% ethanolic (UR95), 50% ethanolic (UR50), and distilled water (URW) extracts of *U. rhynchophylla* with cumulative concentration of 0.0025-0.1575 mg/ml on 1 µM PE pre-contracted isolated endothelium-intact Sprague Dawley (SD) rat aortic rings (n=8) according to an example of the present invention.
Figure 3C:
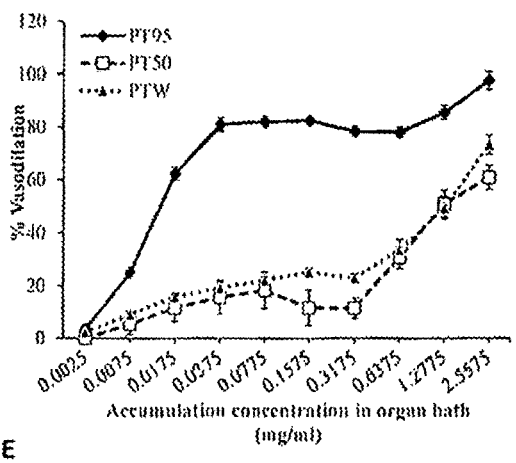
FIG. 3C is a graph illustrating the vasodilatory effect of 95% ethanolic (PT95), 50% ethanolic (PT50), and distilled water (PTW) extracts of *P. thomsonii* with cumulative concentration of 0.0025-2.5575 mg/ml on 1 µM PE pre-contracted isolated endothelium-intact Sprague Dawley (SD) rat aortic rings (n=8) according to an example of the present invention.
Figure 3D:
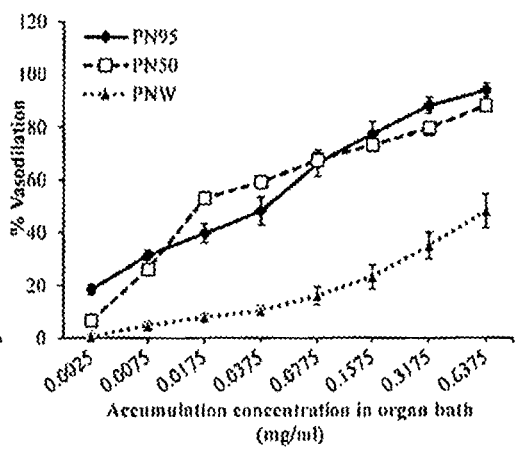
FIG. 3D is a graph illustrating the vasodilatory effect of 95% ethanolic (PN95), 50% ethanolic (PN50), and distilled water (PNW) extracts of *P. notoginseng* with cumulative concentration of 0.0025-0.6375 mg/ml on 1 µM PE pre-contracted isolated endothelium-intact Sprague Dawley (SD) rat aortic rings (n=8) according to an example of the present invention.
Figure 3E:
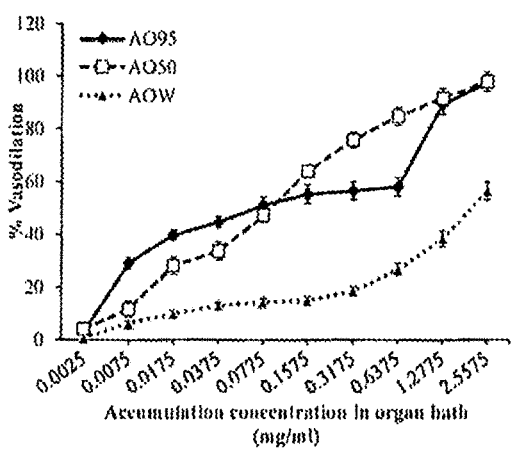
FIG. 3E is a graph illustrating the vasodilatory effect of 95% ethanolic (AO95), 50% ethanolic (AO50), and distilled water (AOW) extracts of *A. orientale* with cumulative concentration of 0.0025-2.5575 mg/ml on 1 µM PE pre-contracted isolated endothelium-intact Sprague Dawley (SD) rat aortic rings (n=8) according to an example of the present invention.

Vasodilatory Effects of Different Herbal Solvent Extracts on PE Pre-Contractile Tone Three types of solvents were used for the herbal extractions: 95% ethanol, 50% ethanol, and distilled water. According to FIG. 3A, the GE95 and GEW showed similar trends of concentration-dependent vasodilatory effects on the isolated aortic rings. However, the GE50 clearly showed the highest vasodilatory effects on the aortic rings compared to other two extracts from the same herb, with lowest $EC_{50}$ and highest $R_{max}$ values as shown in Table 1. According to FIGS. 3B, 3C, and 3D, the UR95, PT95, and PN95 have exhibited the highest vasodilatory effects among the extracts of each herb, and their $EC_{50}$ and $R_{max}$ values are shown in Table 1 as well. The vasodilatory effects of AO95 and AO50 as shown in FIG. 3E have similar $R_{max}$ values. However, the $EC_{50}$ value of AO50 was much lower than that of AO95. Thus, AO50 was considered to have the most potent vasodilatory effects of the three extracts. Generally, GE50, UR95, PT95, PN95, and AO50 were selected for further orthogonal stimulus-response compatibility group screening for vasodilatory effects.

TABLE 1

Comparison of $EC_{50}$ and $R_{max}$ Values Between Different Solvent Extracts of G. elate, U. rhynchophylla, P. thomsonii, P. notoginseng, and A. orientale

| Herbs | Concentrations (mg/mL) | Types of solvent | $EC_{50}$ values (mg/mL) | $R_{max}$ values (%) |
|---|---|---|---|---|
| G. elata | 0.0025-1.28 | 95% ethanol | 0.131 ± 0.027 | 101.07 ± 1.92 |
| | | 50% ethanol | 0.024 ± 0.004 | 106.13 ± 0.91 |
| | | dH$_2$O | 0.105 ± 0.018 | 98.90 ± 2.78 |
| U. rhynchophylla | 0.0025-0.08 | 95% ethanol | 0.025 ± 0.003 | 102.55 ± 6.28 |
| | | 50% ethanol | 0.032 ± 0.006 | 75.33 ± 5.10 |
| | | dH$_2$O | 0.513 ± 0.155 | 52.36 ± 5.22 |
| P. thomsonii | 0.0025-1.28 | 95% ethanol | 0.023 ± 0.003 | 97.69 ± 3.46 |
| | | 50% ethanol | 4.072 ± 1.354 | 61.02 ± 4.58 |
| | | dH$_2$O | 2.587 ± 0.577 | 73.40 ± 3.72 |
| P. notoginseng | 0.0025-0.32 | 95% ethanol | 0.034 ± 0.007 | 94.15 ± 2.79 |
| | | 50% ethanol | 0.031 ± 0.004 | 88.35 ± 0.69 |
| | | dH$_2$O | 0.781 ± 0.214 | 48.27 ± 6.36 |
| A. orientale | 0.0025-1.28 | 95% ethanol | 0.099 ± 0.021 | 97.32 ± 3.20 |
| | | 50% ethanol | 0.085 ± 0.013 | 97.80 ± 3.68 |
| | | dH$_2$O | 33.762 ± 7.539 | 56.41 ± 3.42 |

$EC_{50}$, half of maximal effective concentration;
$R_{max}$, maximal relaxation.
Data are represented as mean ± SEM and plotted in FIG. 3 (n = 8 for each different solvent extract)

Orthogonal Stimulus-Response Compatibility Group Studies

The effective concentrations $EC_0$, $EC_{10}$, $EC_{15}$, $EC_{20}$, and $EC_{25}$ of the GE50, UR95, PT95, PN95, and AO50 extracts were obtained from their respective concentration-response curves and shown in Table 2.

TABLE 2

The Effective Concentration Selected from Concentration-Response Curves of Each Herbal Extract with the Highest Vasodilatory Effect for Orthogonal Stimulus-Response Compatibility Group Screening

| Effective concentration (%) | Concentration (mg/ml) | | | | |
|---|---|---|---|---|---|
| | A | B | C | D | E |
| Without extract | 0 | 0 | 0 | 0 | 0 |
| 10 | 0.254 | 0.722 | 0.238 | 1.028 | 0.253 |
| 15 | 0.348 | 0.886 | 0.381 | 1.542 | 0.395 |
| 20 | 0.477 | 1.086 | 0.610 | 2.313 | 0.618 |
| 25 | 0.653 | 1.331 | 0.976 | 3.470 | 0.965 |

Concentration stated was obtained from the concentration-response curve of each extract that corresponded to respective effective concentration. Concentrations stated are not the final concentration in tissue bath.
A, 50% ethanolic extract of G. elata;
B, 95% ethanolic extract of U. rhynchophylla;
C, 95% ethanolic extract of P. thomsonii;
D, 95% ethanolic extract of P. notoginseng;
E, 50% ethanolic extract of A. orientale.

The compatibility groups were formed using the $L_{25}$ ($5^5$) formula arrangement as shown in Table 3 and the vasodilatory effects were determined on isolated endothelium-intact rat aortic rings.

TABLE 3

Orthogonal Stimulus-Response Compatibility Group Studies

| Experiment | Compatibility groups | | | | | ER (%) | AR (%) | Efficacy (%) |
|---|---|---|---|---|---|---|---|---|
| | A | B | C | D | E | | | |
| 1 | 1 | 1 | 1 | 1 | 1 | 0 | 0 | 0 |
| 2 | 1 | 2 | 2 | 2 | 2 | 40 | 11.23 ± 1.20 | 28 |
| 3 | 1 | 3 | 3 | 3 | 3 | 60 | 15.57 ± 2.50 | 26 |
| 4 | 1 | 4 | 4 | 4 | 4 | 80 | 31.95 ± 2.50 | 40 |
| 5 | 1 | 5 | 5 | 5 | 5 | 100 | 32.78 ± 1.95 | 33 |
| 6 | 2 | 1 | 2 | 3 | 4 | 55 | 7.47 ± 1.73 | 14 |
| 7 | 2 | 2 | 3 | 4 | 5 | 80 | 14.43 ± 2.16 | 18 |
| 8 | 2 | 3 | 4 | 5 | 1 | 70 | 13.07 ± 1.70 | 19 |
| 9 | 2 | 4 | 5 | 1 | 2 | 65 | 11.66 ± 2.80 | 18 |
| 10 | 2 | 5 | 1 | 2 | 3 | 60 | 22.6 ± 1.20 | 38 |
| 11 | 3 | 1 | 3 | 5 | 2 | 65 | 24.49 ± 2.27 | 38 |
| 12 | 3 | 2 | 4 | 1 | 3 | 60 | 12.43 ± 1.48 | 21 |
| 13 | 3 | 3 | 5 | 2 | 4 | 85 | 7.09 ± 0.62 | 8 |

TABLE 3-continued

Orthogonal Stimulus-Response Compatibility Group Studies

| Experiment | Compatibility groups | | | | | ER (%) | AR (%) | Efficacy (%) |
|---|---|---|---|---|---|---|---|---|
| | A | B | C | D | E | | | |
| 14 | 3 | 4 | 1 | 4 | 5 | 75 | 6.5 ± 0.53 | 9 |
| 15 | 3 | 5 | 2 | 4 | 1 | 70 | 10.37 ± 1.93 | 15 |
| 16 | 4 | 1 | 4 | 2 | 5 | 75 | 10.21 ± 1.33 | 14 |
| 17 | 4 | 2 | 5 | 3 | 1 | 70 | 6.8 ± 2.07 | 10 |
| 18 | 4 | 3 | 1 | 4 | 2 | 65 | 32.07 ± 1.71 | 49 |
| 19 | 4 | 4 | 2 | 5 | 3 | 90 | 14.57 ± 1.15 | 16 |
| 20 | 4 | 5 | 3 | 1 | 4 | 80 | 12.05 ± 1.97 | 15 |
| 21 | 5 | 1 | 5 | 4 | 3 | 85 | 4.79 ± 1.18 | 6 |
| 22 | 5 | 2 | 1 | 5 | 4 | 80 | 8.53 ± 1.39 | 11 |
| 23 | 5 | 3 | 2 | 1 | 5 | 75 | 9.78 ± 0.99 | 13 |
| 24 | 5 | 4 | 3 | 2 | 1 | 70 | 10.12 ± 1.97 | 14 |
| 25 | 5 | 5 | 4 | 3 | 2 | 95 | 17.61 ± 2.21 | 19 |

Concentration used in orthogonal stimulus-response compatibility group screening: 1, $EC_0$; 2, $EC_{10}$; 3, $EC_{15}$; 4, $EC_{20}$; 5, $EC_{25}$; derived from Table 2. Efficacy, (AR/ER) · 100%; ER, expected relaxation; AR, actual relaxation; A, 50% ethanolic extract of G. elata; B, 95% ethanolic extract of U. rhynchophylla; C, 95% ethanolic extract of P. thomsonii; D, 95% ethanolic extract of P. notoginseng; E, 50% ethanolic extract of A. orientale. Data are represented as mean ± SEM (n = 6 for each experiment).

Then, the average relaxation of GE50, UR95, PT95, PN95, and AO50 that corresponds to their EC was further calculated and stated in Table 4.

TABLE 4

Average Relaxation of Aortic Rings Obtained from Orthogonal Stimulus-Response Compatibility Group Screening

| Effective Concentration | Average relaxation (%) | | | | |
|---|---|---|---|---|---|
| | A | B | C | D | E |
| 0 | 18.31 | 9.39 | 13.94 | 9.18 | 8.07 |
| 10 | 13.85 | 10.68 | 10.68 | 12.25 | 19.41 |
| 15 | 12.18 | 15.52 | 15.33 | 10.79 | 13.99 |
| 20 | 15.14 | 14.96 | 17.05 | 18.72 | 13.42 |
| 25 | 10.17 | 19.08 | 12.62 | 18.69 | 14.74 |

A, 50% ethanolic extract of G. elata;
B, 95% ethanolic extract of U. rhynchophylla;
C, 95% ethanolic extract of P. thomsonii;
D, 95% ethanolic extract of P. notoginseng;
E, 50% ethanolic extract of A. orientale.

The results showed that the highest average relaxation of GE50, UR95, P195, PN95, and AO50 was achieved at $EC_0$, $EC_{25}$, $EC_{20}$, $EC_{20}$, and $EC_{10}$ (named as F1), respectively. The potency of F1 was further confirmed by comparing it with F2 and F3. The efficacy of their vasodilatory effects is shown in Table 5. With F1 exhibiting the highest efficacy at 51%, it once again proved its highest potency in exerting vasodilatory effect on the isolated endothelium-intact rat aortic rings, thus it was used for further analysis.

TABLE 5

Confirmation Test on Optimum Combination Ratio of Herbal Extracts in Exerting Highest Vasodilatory Effects

| Formulae | Optimum combination ratio | | | | | ER (%) | AR (%) | Efficacy (%) |
|---|---|---|---|---|---|---|---|---|
| | A | B | C | D | E | | | |
| F1 | $EC_0$ | $EC_{25}$ | $EC_{20}$ | $EC_{20}$ | $EC_{10}$ | 75 | 38.15 ± 2.05 | 51 |
| F2 | $EC_0$ | $EC_{25}$ | $EC_{20}$ | $EC_{25}$ | $EC_{10}$ | 80 | 11.79 ± 2.05 | 15 |
| F3 | $EC_0$ | $EC_{25}$ | $EC_{20}$ | $EC_{20}$ | $EC_{10}$ | 95 | 11.18 ± 1.01 | 12 |

Efficacy, (AR/ER) · 100%; A, 50% ethanolic extract of G. elata; B, 95% ethanolic extract of U. rhynchophylla; C, 95% ethanolic extract of P. thomsonii; D, 95% ethanolic extract of P. notoginseng; E, 50% ethanolic extract of A. orientale. Data are represented as mean ± SEM (n = 8 for each formula).

Figure 4:
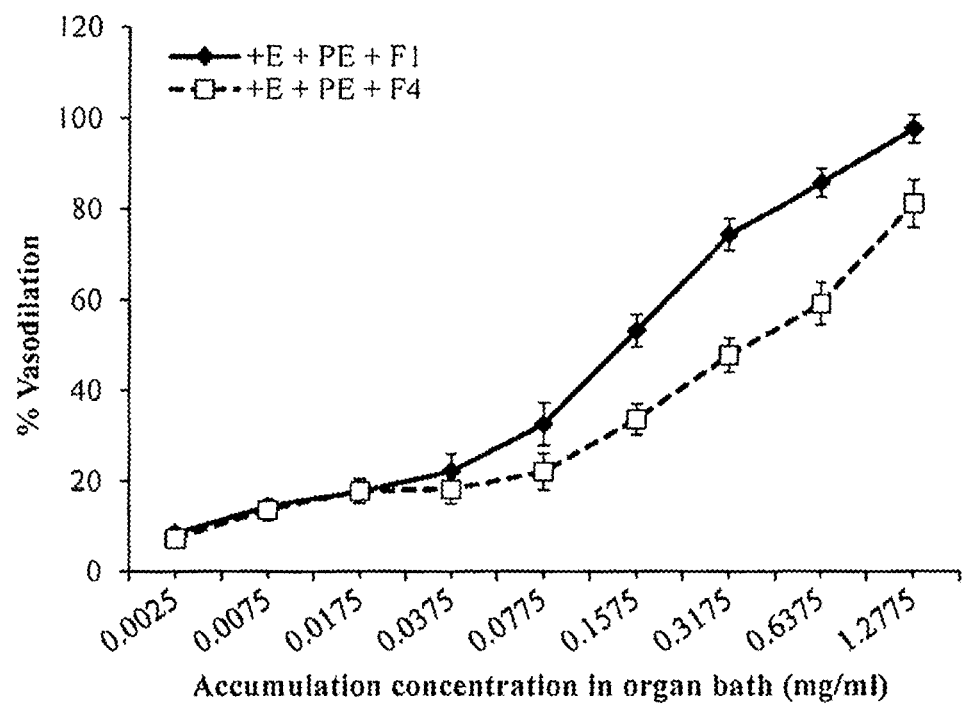
FIG. 4 is a graph illustrating vasodilatory effects of F1 (extracts GE50, UR95, PT95, PN95, and AO50 combined in EC: 0, 25, 20, 20, and 10, respectively) and F4 (extracts GE50, UR95, PT95, PN95, and AO50 combined in EC: 20, 15, 0, 20, and 10, respectively) in cumulative concentration of 0.0025-1.2275 mg/ml on 1 µM PE pre-contracted isolated endothelium-intact SD rat aortic rings (n=8) according to an example of the present invention.

The potency of F1 was further assured by comparing it with the 18th compatibility group (named as F4) with 49% efficacy. FIG. 4 shows that the concentration-response curve of vasodilatory effects of F1 was much higher than F4 at a final concentration of 1.2775 mg/ml with $EC_{50}$ and $R_{max}$ values shown in Table 6.

TABLE 6

The $EC_{50}$ and $R_{max}$ Values of Different Solvent Extracted Formulae

| Formulae | Doses (mg/ml) | $EC_{50}$ values (mg/ml) | $R_{max}$ values (%) |
|---|---|---|---|
| F1 | 0.0025-0.64 | 0.104 ± 0.014 | 97.80 ± 3.12 |
| F4 | 0.0025-0.64 | 0.225 ± 0.010 | 81.28 ± 5.25 |
| F1-1 | 0.0025-1.28 | 0.250 ± 0.101 | 95.77 ± 2.75 |
| F1-2 | 0.0025-0.16 | 0.028 ± 0.005 | 101.71 ± 3.64 |
| F1-3 | 0.0025-1.28 | 0.254 ± 0.067 | 93.25 ± 3.98 |
| F1-4 | 0.0025-1.28 | 0.171 ± 0.022 | 99.69 ± 2.12 |
| F1-5 | 0.0025-1.28 | 0.377 ± 0.124 | 92.74 ± 3.38 |

F1, extracts A, B, C, D, and E combined in EC: 0, 25, 20, 20, and 10, respectively.
F4, extracts A, B, C, D, and E combined in EC: 20, 15, 0, 20, and 10, respectively.
F1-1, distilled water extract of five herbs using F1 ratio at 50° C.;
F1-2, 50% ethanolic extract of five herbs using F1 ratio at 50° C.;
F1-3, 95% ethanolic extract of five herbs using F1 ratio at 50° C.;
F1-4, total 95% of ethanolic extraction of U. rhynchophylla, P. thomsonii, and P. notoginseng (F1 ratio) combined with D (F1 ratio) at 50° C.;
F1-5, distilled water extract of five herbs following F1 ratio at 100° C.
$EC_{50}$, half of maximal effective concentration;
$R_{max}$, maximal relaxation.
A, 50% ethanolic extract of G. elata;
B, 95% ethanolic extract of U. rhynchophylla;
C, 95% ethanolic extract of P. thomsonii;
D, 95% ethanolic extract of P. notoginseng;
E, 50% ethanolic extract of A. orientale.
Data are represented as mean ± SEM and plotted in FIG. 4 and 5 (n = 8 for each formula).

Vasodilatory Effects of Different Solvent Extracts of F1 Formula

Figure 5:
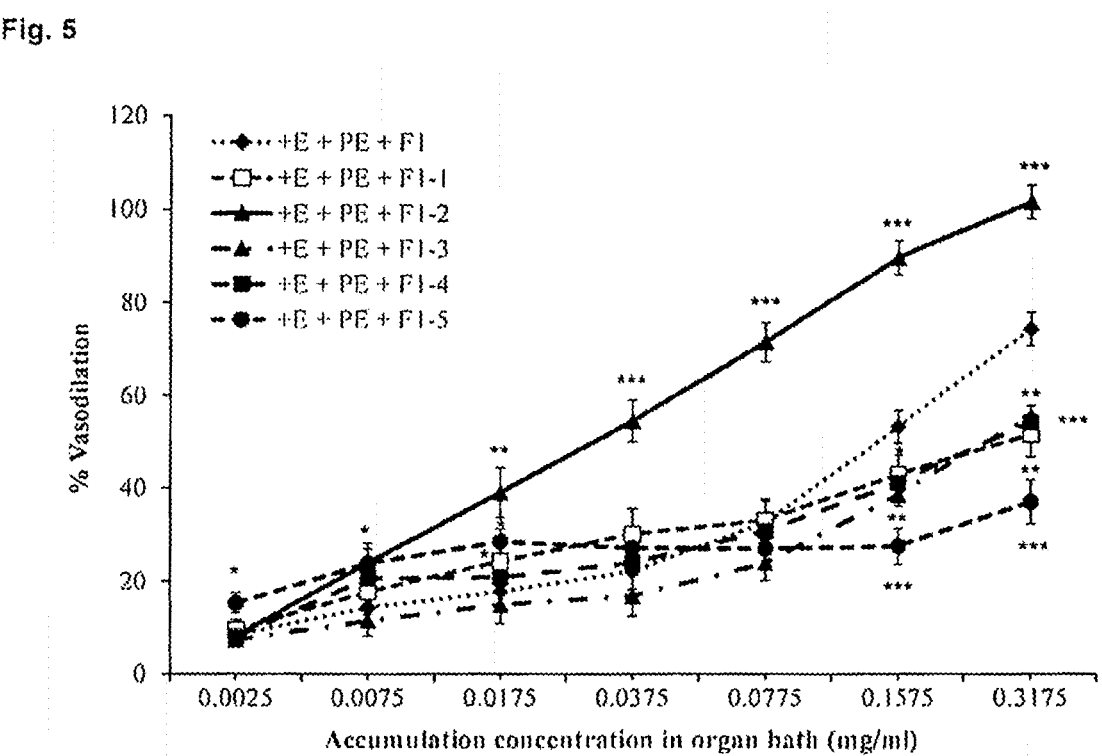
FIG. 5 is a graph illustrating vasodilatory effects of F1, F1-1, F1-2, F1-3, F1-4, and F1-5 with cumulative concentration of 0.0025-0.3175 mg/ml on 1 µM PE pre-contracted isolated endothelium-intact SD rat aortic rings (n=8) according to an example of the present invention.

F1 was further analyzed by using different preparation and solvent extraction methods as described previously in the Materials and Methods section. The cumulative concentrations of F1, F1-1, F1-2, F1-3, F1-4, and F1-5 (0.0025-0.3175 mg/mL in tissue bath) were applied to the isolated endothelium-intact rat aortic rings and the resulting concentration-response curves were compared among each other, as shown in FIG. 5. All formulae elicited concentration-dependent vasodilatory effects on the isolated aortic rings. The $EC_{50}$ and $R_{max}$ values of F1-1, F1-3, F1-4, and F1-5 were mildly significant (P<0.05) compared to F1. However, F1-2 has dramatically increased the $R_{max}$ value to 101.71%±3.64% with a final concentration of 0.3175 mg/ml and the lowest $EC_{50}$ value at 0.028±0.005 mg/ml (P<0.05), which indicated it is the most effective in terms of vasodilatory effects compared to the other F1 derivatives.

EXAMPLE 2

In Vitro Test on Mechanism of Actions of F1-2
Materials and Methods
Plants and Chemicals The PE and Ach were purchased from Acros Organics (Belgium). 4-AP was purchased from Merck (Germany). Ethylene glycol tetraacetic acid (EGTA) and MB were purchased from Promedipharm Sdn. Bhd. (Malaysia). Propranolol, L-NAME, atropine, TEA, and $BaCl_2$ were bought from Sigma Aldrich (USA). All these chemicals were dissolved by using distilled water. Whereas, 2-APB, ODQ, and indomethacin which purchased from Sigma Aldrich (USA), and nifedipine from Acros Organics (Belgium) were dissolved by using <1% of Tween 80. Additionally, the carboxymethyl cellulose (CMC) was purchased from the Fisher Scientific UK Ltd. (Loughborough, UK) and was prepared in boiling water at 0.5% (w/v), and kept in refrigerator for further use. The propranolol tablet (40 mg) was purchased from Sunway Pharmaceutical Sdn. Bhd. (Johor, Malaysia). All the chemicals were kept in freezer (Pensonic, PFZ-230) at −20° C., and would be prepared to their respective concentration upon usage.

Animals

Male SHRs weighing between 180-250 g were obtained from the USM ARASC under guideline of USM/Animal Ethics Approval/2016/(103) (786).

Vasodilatory Effect of F1-2 in Endothelium-Denuded Aortic Rings

The intima layer of the isolated aortic rings was removed manually and carefully by using stainless stick. After that, the completeness of the denuded endothelium was assured by exposing the aortic ring to Ach (1 µM) with absolutely no relaxation occurring. Subsequently, PE (1 µM) was added into the tissue bath and left for at least 30 minutes until a plateau stage was achieved. Then, the 100 µl of F1-2 (0.25-16 mg/ml) were added into tissue baths at 20 minutes interval. The cumulative concentration-response curve was constructed, and the $EC_{50}$ and $R_{max}$ values were recorded and compared to the control.

Vasodilatory Effect of F1-2 on KCl Pre-Contracted Aortic Rings

The endothelium-intact isolated aortic rings were pre-contracted with 80 mM of KCl, and left for 30 minutes until a plateau stage was achieved. Then, the 100 µl of F1-2 (0.25-16 mg/ml) were added into tissue baths at 20 minutes interval. The cumulative concentration-response curve was constructed, and the $EC_{50}$ and $R_{max}$ values were recorded and compared to the control.

Roles of EDRFs in F1-2 Vasodilation

The non-selective antagonists of eNOS and COX such as L-NAME (10 µM) and indomethacin (10 µM) respectively were added into the tissue bath separately for 20 minutes incubation with the endothelium-intact isolated aortic rings before the PE pre-contraction. Down the NO-signaling cascade, there are two major vasodilatory-mediating components such as sGC and cGMP, their selective blockers such as ODQ (1 µM) and MB (10 µM) respectively were incubated separately with the mounted endothelium-intact isolated aortic rings for 20 minutes before the PE pre-contraction. After PE pre-contraction, the 100 µl of F1-2 (0.25-16 mg/ml) were added into tissue baths at 20 minutes interval. The cumulative concentration-response curve was constructed, and the $CC_{50}$ and $R_{max}$ values were recorded and compared to the control.

Roles of GPCRs in F1-2 Vasodilation

The $β_2$-adrenergic and muscarinic receptors were studied by pre-incubating the endothelium-intact isolated aortic rings with their non-selective blockers such as propranolol (1 µM) and atropine (1 µM), respectively for 20 minutes before the PE pre-contraction. After PE pre-contraction, the 100 µl of F1-2 (0.25-16 mg/ml) were added into tissue baths at 20 minutes interval. The cumulative concentration-response curve was constructed, and the $EC_{50}$ and $R_{max}$ values were recorded and compared to the control.

Roles of Potassium Channels in F1-2 Vasodilation

There were four types of potassium channels being investigated including $K_{ATP}$, $K_v$, $K_{ca}$, and $K_{ir}$ channels by using glibenclamide (10 µM), 4-AP (1 mM), TEA (1 mM), and $BaCl_2$ (10 µM), respectively. The antagonists were incubated separately with the endothelium-intact isolated aortic rings for 20 minutes before PE pre-contraction. After PE pre-contraction, the 100 µl of F1-2 (0.25-16 mg/ml) were added into tissue baths at 20 minutes interval. The cumulative concentration-response curve was constructed, and the $EC_{50}$ and $R_{max}$ values were recorded and compared to the control.

Roles of Voltage-Operated Calcium Channel (VOCC) in F1-2 Vasodilation

Basically, there were three sets of experiments performed in this mechanism study including the positive control sets by applying three different concentrations of nifedipine (0.1, 0.3, and 1 µM), control set (without treatment), and experimental sets by applying three different concentrations of F1-2 (100 µl of 0.5, 2, and 8 mg/ml, separately, which equals to final concentration of 0.005, 0.02, and 0.08 mg/ml in tissue bath), in the endothelium-intact isolated aortic rings. The $Ca^{2+}$-free high $K^+$ Krebs' solution (11.9 mM $NaHCO_3$, 1.05 mM $MgSO_4$, 91.04 mM NaCl, 50.0 mM KCl, and 5.5 mM glucose, pH 7.4) was used as buffer solution instead of normal Krebs' solution. The experiment started by rinsing the mounted aortic rings with normal Krebs' solution for 3 times at 10 minutes interval. After that, the aortic rings were rinsed with EGTA (0.2 mM) contained $Ca^{2+}$-free high $K^+$ Krebs' solution for 10 minutes to eradicate the $Ca^{2+}$ residue, followed by rinsing with $Ca^{2+}$-free high $K^+$ Krebs' solution for twice at 10 minutes intervals. The resting potential was re-adjusted to 1.0 g before the application of any chemicals. In the control set, $CaCl_2$ was added cumulatively (0.01-10 mM) into the tissue bath at 3 minutes interval. In positive control set, the nifedipine was added into the tissue bath and incubated for 20 minutes before the addition of $CaCl_2$. In the experimental groups, the F1-2 was added into tissue baths for 20 minutes before the addition of $CaCl_2$. After that, the concentration-response curves were constructed, and maximum contraction ($C_{max}$) values were recorded and compared to each other.

Roles of Inositol Triphosphate Receptor ($IP_3R$) in F1-2 Vasodilation

Similar with the VOCC mechanism study, three sets of experiments were carried out for investigating $IP_3R$ including the positive control set by applying the 2-APB (100 µM), control set (without treatment), and experimental sets by applying F1-2 (100 µl of 0.5, 2, and 8 mg/ml, separately, which equals to final concentration of 0.005, 0.02, and 0.08 mg/ml in tissue bath), in the endothelium-denuded isolated aortic rings. Similar protocol as elaborated in VOCC mechanism study was used to investigate this mechanism study. The only step different from VOCC mechanism study was the cumulative addition of $CaCl_2$ was replaced by adding PE (1 µM) and left for 20 minutes to induce transient contraction after the 20 minutes pre-incubation with either 2-APB (positive control), F1-2 (experimental sets). The $C_{max}$ values were recorded and compared among each other.

Preparation of F1-2 for Oral Administration

All the orally administrated drugs were freshly prepared on the day the experiment was carried out. Thirty male SHRs were divided into five groups (n=6 per group) as such negative control, positive control (80 mg/kg of propranolol), and experimental groups (three different dosages for different groups). The weight, systolic BP, diastolic BP, and MAP of all SHRs in five groups were determined before the experiment was carried out and assigned as results for week 0. The negative control group of SHRs was treated with 5 ml/kg of distilled water. The positive control group was treated with 80 mg/kg of propranolol. The experimental groups were treated with 0.24273 (small dose), 0.48546 (medium dose), and 0.97092 g/kg (high dose) of F1-2, separately. Propranolol and F1-2 were prepared by dissolving in 0.5% of CMC prior to the administration. All drugs were orally administrated by using the 14-sized curved feeding needle (Kent Scientific Corporation, Torrington, Conn., USA) every morning after eight hours of fasting the night before, and were treated for 28 days consecutively with their weight, systolic BP, diastolic BP, and MAP measured once a week.

Measurements of SBP, DBP, and MAP

The SBP, DBP, and MAP were measured by using tail-cuff method with the non-invasive blood pressure measurement system, CODA (Kent Scientific Corporation, Torrington, Conn., USA) which was equipped with a controller, laptop CODA software, cuffs, animal restrainers, infrared warming pads, and infrared thermometer. The measurements were performed by the same researcher at the same daytime once weekly. Before the experiments commenced, the SHRs were housed in the restrainer according to their body size and pre-warmed on the warming plate at 32° C. and were covered by warming blanket for at least 15 minutes to intensify the pulsation of the tail artery. The measurements were repeated at least twice for each SHR to obtain at least six accepted measurements (n=6) by the CODA program. The obtained SBP, DBP, MAP of positive control and experimental groups were compared to the negative control.

Statistical Analysis

All the data were expressed as mean±S.E.M. The results obtained for antagonists pre-treated groups were compared to the control by using one-way ANOVA, and post-hoc Dunnett's test with the use of SPSS version 22 software. All tests were two-tailed and the significance rejection value was fixed at P<0.05.

Results

First Line Screening on F1-2 Vasodilation

Figure 6:
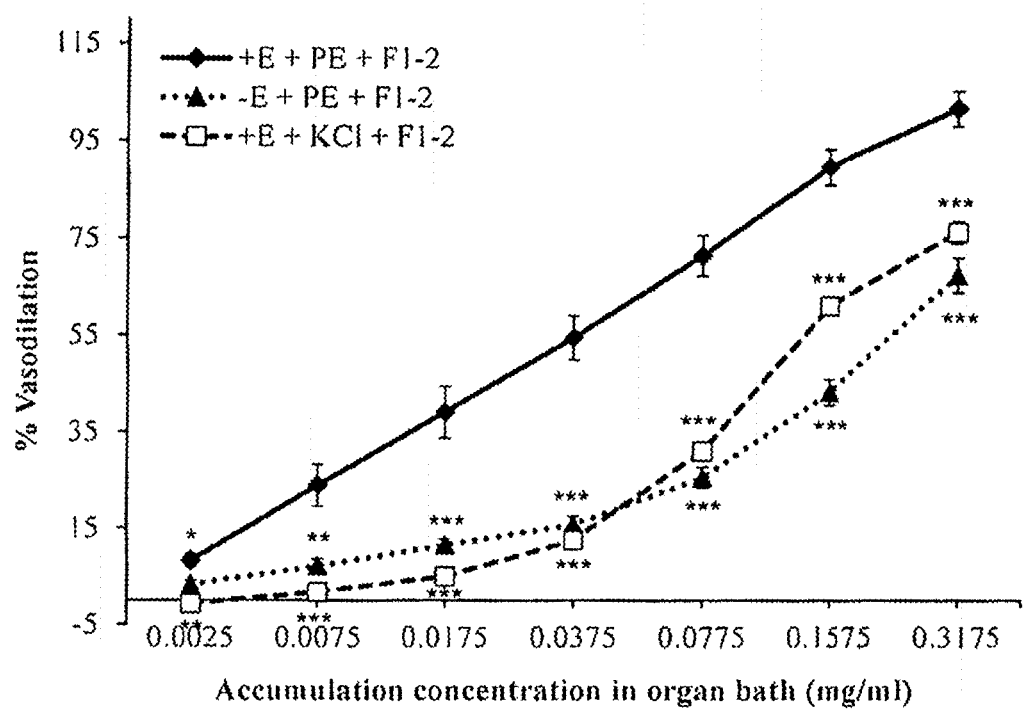
FIG. 6 is a graph illustrating cumulative concentration-response curves of F1-2 vasodilatory effects on PE pre-contracted endothelium-intact aortic rings (control) compared to the vasodilatory effects exerted by F1-2 on the PE pre-contracted endothelium-denuded aortic rings or KCl-primed endothelium-intact aortic rings. (+E: endothelium-intact aortic rings; −E: endothelium-denuded aortic rings; *: $P<0.05$; : $P<0.01$; *: $P<0.001$; n=8).

Basically, the vascular response of F1-2 which was added cumulatively on PE pre-contracted endothelium-intact rat aortic rings was in concentration-dependent manner, and the $EC_{50}$ and $R_{max}$ values were obtained at 0.028±0.005 mg/ml and 101.71±3.64%, respectively. This result was assigned as the control in this mechanism studies. Here, the first line screening has included both the endothelium-dependency and channel-linked receptors pathways determination for vasodilatory effects of F1-2. According to FIG. 6, in the condition of endothelium-impaired aortic rings, there was approximately 33% of $R_{max}$ value reduction compared to the control, while the $EC_{50}$ value (P<0.001) was shown in Table 6. Moreover, approximately one quarter of $R_{max}$ value of F1-2 was significantly suppressed on the 80 mM KCl-primed aortic rings compared to the PE-primed, whereas the $EC_{50}$ value was significantly increased (P<0.001). This implied the involvement of both the endothelium-independent and channel-linked receptors mechanism pathways, where both were in concentration-dependent manner.

Roles of EDRFs and NO-Signaling Cascade in F1-2 Vasodilation

Figure 7:
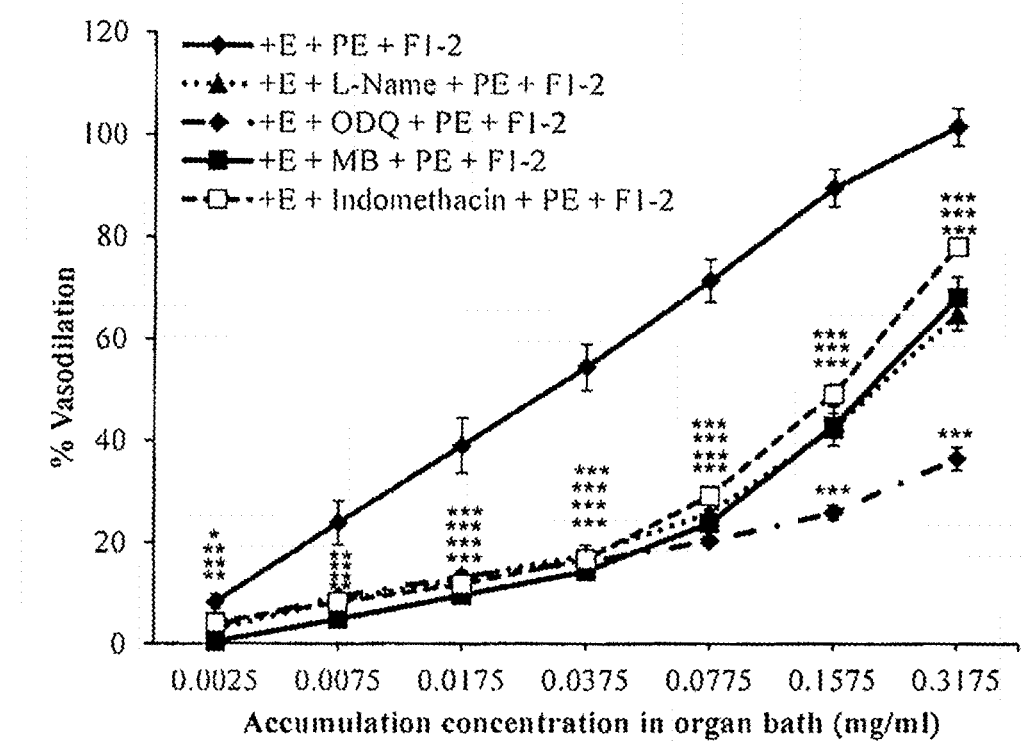
FIG. 7 is a graph illustrating cumulative concentration-response curves of F1-2 vasodilatory effects on PE pre-contracted endothelium-intact aortic rings (control) compared to vasodilatory effects exerted by F1-2 upon L-NAME, ODQ, MB, or indomethacin pre-treated PE pre-contracted endothelium-intact aortic rings (+E: endothelium-intact aortic rings; *: $P<0.05$; : $P<0.01$; *: $P<0.001$; n=8).

As shown in FIG. 7, the presence of L-NAME and indomethacin in their respective experimental groups had markedly attenuated the vasodilatory effect of F1-2 compared to the control with $EC_{50}$ values increased to 0.396±0.110 (P<0.001) and 0.168±0.021 mg/ml (P<0.001), respectively (Table 6). The results indicated that NO could play a major role in F1-2 endothelium-dependent vasodilatory activity more than the $PGI_2$. Furthermore, down the NO-signaling cascade, the selective antagonists ODQ and MB had dramatically reduced the vasodilatory effect of F1-2 in their tissue baths, respectively. However, the $EC_{50}$ value obtained when ODQ present was markedly increased up to 13.710±4.370 mg/ml (P<0.001) compared to control, hence indicating its pivotal role in eliciting F1-2-mediated vasodilatory effect.

Roles of GPCRs in F1-2 Vasodilation

Figure 8:
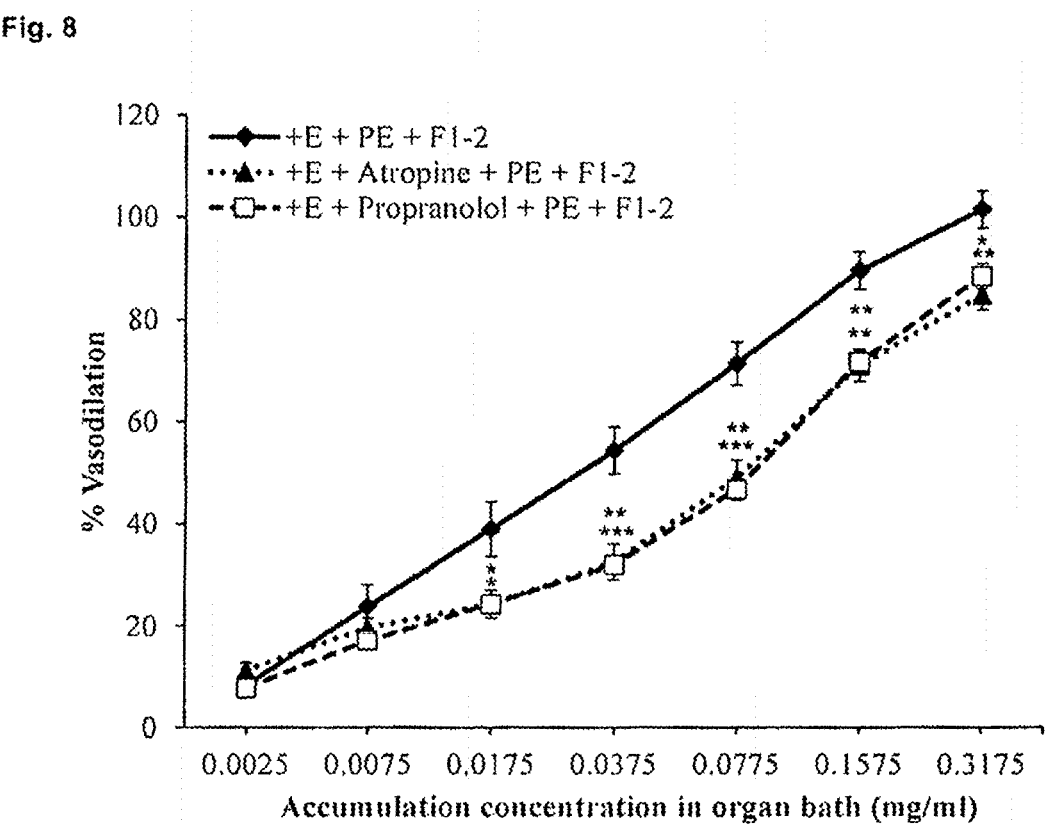
FIG. 8 is a graph illustrating cumulative concentration-response curves of F1-2 vasodilatory effects on PE pre-contracted endothelium-intact aortic rings (control) compared to the vasodilatory effects exerted by F1-2 upon atropine or propranolol pre-treated PE pre-contracted endothelium-intact aortic rings (+E: endothelium-intact aortic rings; *: $P<0.05$; : $P<0.01$; *: $P<0.001$; n=8).

From the results obtained during the primary screening, the vasodilatory activity exerted by F1-2 was suggested to be partially attributed to the endothelium-independent relaxing factor such as $G_s\alpha$ protein-coupled $\beta_2$-adrenergic receptor which have often been considered as one of the major endothelium-independent relaxing factor. According to FIG. 8, the vasodilatory effect of F1-2 in the presence of propranolol was significantly inhibited with dramatic increase of $EC_{50}$ value to 0.060±0.005 mg/ml (P<0.001) compared to control as shown in Table 6. Moreover, the non-selective blocker, atropine had abundantly suppressed (P<0.01) the vasodilatory effect of F1-2 on the PE-primed aortic rings. The trend of inhibition resembled the inhibitory effect of propranolol, but to a lesser extent, as shown in FIG. 8. The result indicated the participation of both GPCRs in the F1-2-mediated vasodilatory action.

Roles of Potassium Channels in F1-2 Vasodilation

Figure 9:
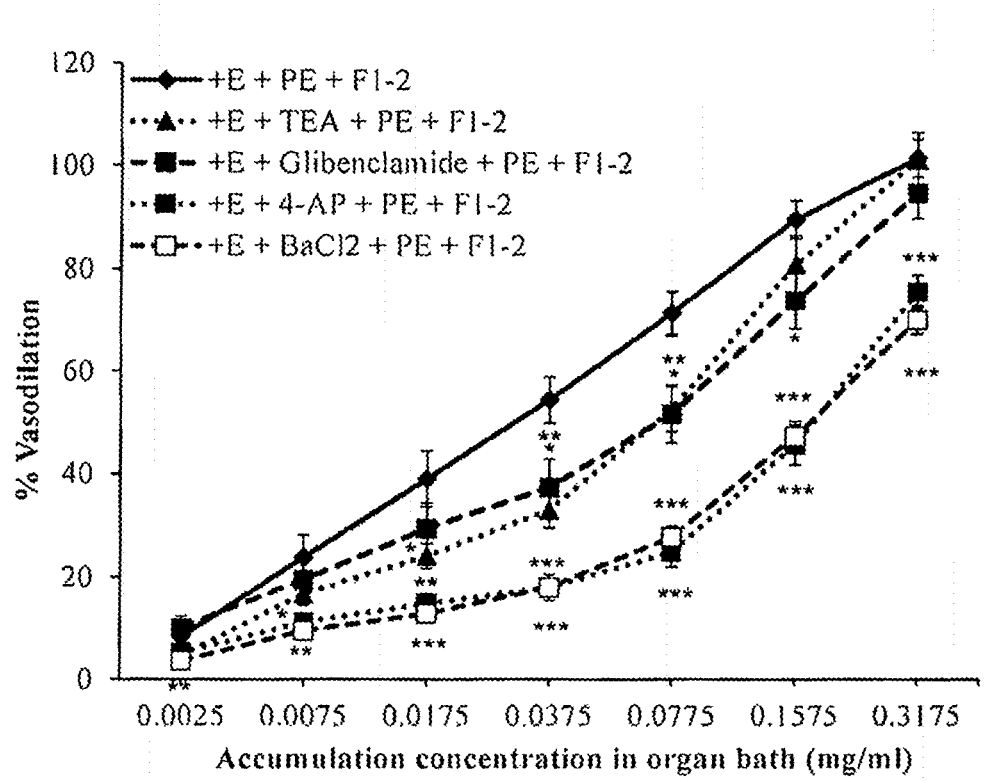
FIG. 9 is a graph illustrating cumulative concentration-response curves of F1-2 vasodilatory effects on PE pre-contracted endothelium-intact aortic rings (control) compared to the vasodilatory effects exerted by F1-2 upon TEA, glibenclamide, 4-AP, or BaCl$_2$ pre-treated PE pre-contracted endothelium-intact aortic rings (+E: endothelium-intact aortic rings; *: $P<0.05$; **: $P<0.01$; $P<0.001$; n=8).

As shown in FIG. 9, the vasodilatory effect of F1-2 was markedly attenuated during the presence of 4-AP and $BaCl_2$ in their respective tissue baths, thus, their $EC_{50}$ values were significantly increased to 0.282±0.089 (P<0.001) and 0.248±0.047 mg/ml (P<0.001), respectively. Similarly, the presence of TEA and glibenclamide in their respective experimental groups had significantly suppressed the vasodilatory activity of F1-2, hence $EC_{50}$ values were increased abundantly to 0.057±0.015 (P<0.01) and 0.060±0.015 (P<0.05), respectively (Table 6). However, the trend of inhibition for both antagonists were similar where their antagonizing effect started to decline at F1-2 cumulative concentration of 0.1575 mg/ml, therefore the $R_{max}$ values obtained were slightly reduced to 101.48±5.27 and 94.88±4.93% for TEA and glibenclamide, respectively. The significance of antagonizing effect could be arranged according to their $EC_{50}$ values as such: 4-AP>$BaCl_2$>glibenclamide>TEA, as shown in Table 6.

TABLE 6

Significance of $EC_{50}$ values and comparison of $R_{max}$ values obtained from the cumulative concentration-response curves under different pre-treatments in vasodilatory effect of F1-2.

| Treatments | $EC_{50}$ Values (mg/ml) | $R_{max}$ Values (%) | One Way ANOVA (P values) |
|---|---|---|---|
| First line screening | | | |
| Control | 0.028 ± 0.005 | 101.71 ± 3.64 | — |
| KCl | 0.145 ± 0.013 | 76.31 ± 2.28 | <0.001 |
| Denuded | 0.370 ± 0.117 | 67.39 ± 3.59 | <0.001 |

TABLE 6-continued

Significance of $EC_{50}$ values and comparison of $R_{max}$ values obtained from the cumulative concentration-response curves under different pre-treatments in vasodilatory effect of F1-2.

| Treatments | $EC_{50}$ Values (mg/ml) | $R_{max}$ Values (%) | One Way ANOVA (P values) |
|---|---|---|---|
| EDRFs and NO cascade mechanisms | | | |
| L-NAME | 0.396 ± 0.110 | 64.91 ± 3.10 | <0.001 |
| ODQ | 13.710 ± 4.370 | 36.60 ± 2.23 | <0.001 |
| MB | 0.456 ± 0.183 | 68.22 ± 4.06 | <0.001 |
| Indomethacin | 0.168 ± 0.021 | 78.19 ± 1.58 | <0.001 |
| GPCRs | | | |
| Atropine | 0.069 ± 0.015 | 84.96 ± 2.99 | <0.01 |
| Propranolol | 0.060 ± 0.005 | 88.62 ± 2.48 | <0.001 |
| Potassium channel-linked receptors | | | |
| TEA | 0.057 ± 0.015 | 101.48 ± 5.27 | <0.01 |
| Glibenclamide | 0.060 ± 0.015 | 94.88 ± 4.93 | <0.05 |
| 4-AP | 0.282 ± 0.089 | 75.64 ± 3.27 | <0.001 |
| $BaCl_2$ | 0.248 ± 0.047 | 70.17 ± 2.73 | <0.001 |

$EC_{50}$: half of effective concentration;
EDRFs: endothelium-derived relaxing factors;
GPCRs: G protein-coupled receptors;
$R_{max}$: maximal relaxation;
number of determination: n-8.

Roles of VOCC and $IP_3R$ in F1-2 Vasodilation

Figure 10A:
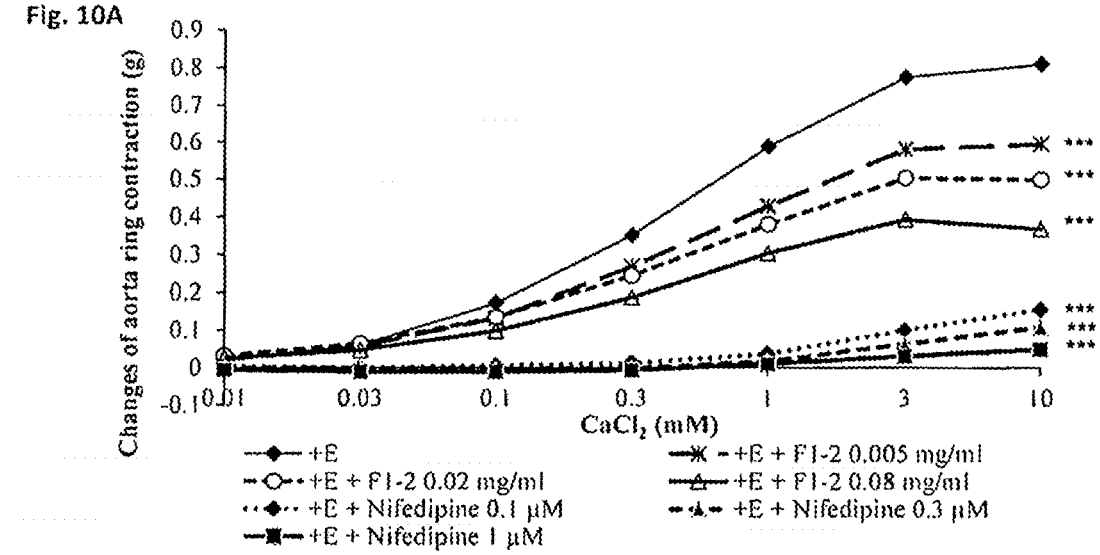
FIG. 10A is a graph illustrating the vasoconstriction response-curves obtained from cumulative addition of CaCl$_2$ on untreated endothelium-intact aortic rings (control) compared to nifedipine (0.1, 0.3, and 1 µM) or F1-2 (0.005, 0.02, and 0.08 mg/ml) pre-treated endothelium-intact aortic rings (*: $P<0.05$; : $P<0.01$; *: $P<0.001$; n=8).

According to Table 7, the influx of calcium into the cytosol in the control group, the $C_{max}$ value obtained was 0.811±0.069 g. Pre-incubation of the endothelium-intact aortic VOCC selective blocker, nifedipine (0.1, 0.3, 1 μM) had dramatically suppressed at least 80% of the contractile tone, and almost abolished the contraction tension upon the pre-incubation with 1 μM of nifedipine compared to control. Similar significance (P<0.001) of the blocking effect was exerted by F1-2 at all the three concentrations (0.005-0.08 mg/ml), but to a lesser extent compared to nifedipine as shown in FIG. 10A. The blocking effect of F1-2 on the vasoconstriction was enhanced gradually with increasing concentration of pre-incubated F1-2. A maximum of 51% of contraction tone was abolished compared to the control when the endothelium-intact aortic rings were pre-incubated with 0.08 mg/ml of F1-2 (P<0.001). The $C_{max}$ values achieved upon each treatment were shown in Table 7.

Figure 10B:
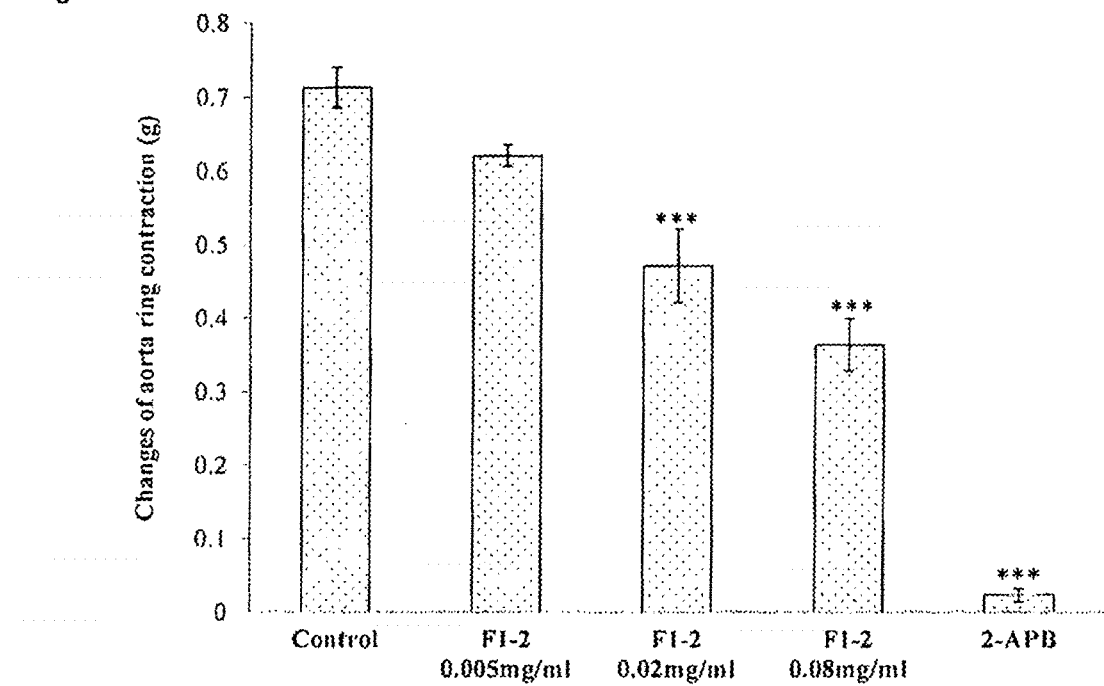
FIG. 10B is a graph illustrating the vasoconstriction response induced by PE on untreated endothelium-denuded aortic rings (control) compared to 2-APB (100 µM) or F1-2 (0.005, 0.02, and 0.08 mg/ml) pre-treated endothelium-denuded aortic rings (*: $P<0.05$; : $P<0.01$; *: $P<0.001$; n=8).

Furthermore, FIG. 10B showed the pre-incubation of 2-APB with the endothelium-denuded aortic rings had abolished approximately 97% (P<0.001) of the contraction tension compared to control that originally has a $C_{max}$ value of 0.714±0.027 g, as shown in the Table 7. Low concentration of F1-2 (0.005 mg/ml) did not give any clear-cut inhibitory effect on the PE-induced contraction tone. However, the increasing concentration of F1-2 applied significantly reduced up to 50% (P<0.001) of contraction tension compared to control. The antagonistic effect of F1-2 at both VOCC and $IP_3R$ was in concentration-dependence manner.

TABLE 7

Comparison of $C_{max}$ values among different treatments on calcium channels mechanism studies in F1-2.

| Treatments | $C_{max}$ Values (g) | One Way ANOVA (P values) |
|---|---|---|
| VOCC | | |
| Control | 0.811 ± 0.069 | — |
| 0.1 μM Nif | 0.155 ± 0.010 | <0.001 |
| 0.3 μM Nif | 0.108 ± 0.008 | <0.001 |
| 1 μM Nif | 0.049 ± 0.007 | <0.001 |
| 0.005 mg/ml F1-2 | 0.598 ± 0.016 | <0.001 |
| 0.02 mg/ml F1-2 | 0.506 ± 0.016 | <0.001 |
| 0.08 mg/ml F1-2 | 0.395 ± 0.019 | <0.001 |
| $IP_3R$ | | |
| Control | 0.714 ± 0.027 | — |
| 100 μM 2-APB | 0.024 ± 0.009 | <0.001 |
| 0.005 mg/ml F1-2 | 0.621 ± 0.015 | >0.05 |
| 0.02 mg/ml F1-2 | 0.472 ± 0.050 | <0.001 |
| 0.08 mg/ml F1-2 | 0.364 ± 0.035 | <0.001 | number of determination: n = 8.

Measurement of SBP, DBP, and MAP on F1-2-Treated SHRs

Figure 11A:
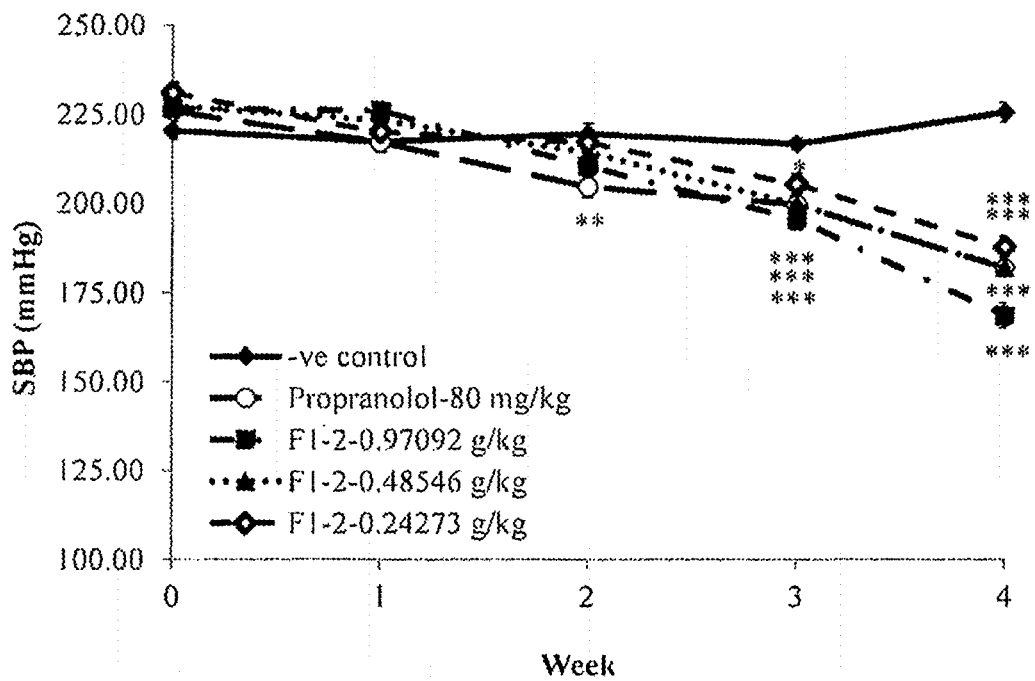
FIG. 11A is a graph illustrating the antihypertensive effect of 0.97092 g/kg (high dose), 0.48546 g/kg (medium dose), and 0.24273 g/kg (small dose) of F1-2, and 80 mg/kg propranolol (positive control) on systolic blood pressure (SBP) of SHRs during 28 days of oral administration and compared to the control group (*: $P<0.05$; : $P<0.01$; *: $P<0.001$; Mean±S.E.M.; n=6).
Figure 11B:
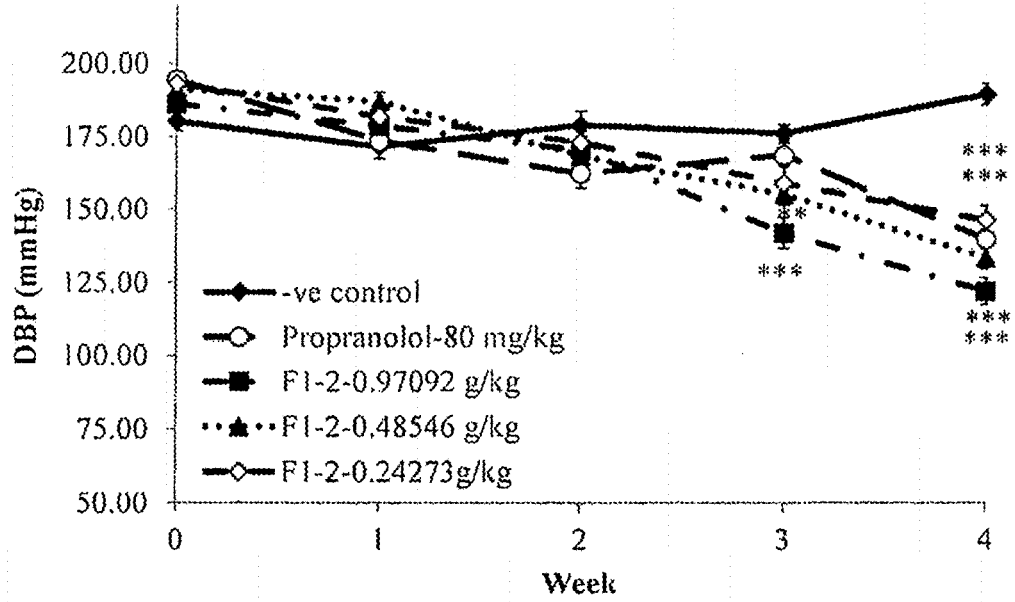
FIG. 11B is a graph illustrating the antihypertensive effect of 0.97092 g/kg (high dose), 0.48546 g/kg (medium dose), and 0.24273 g/kg (small dose) of F1-2, and 80 mg/kg propranolol (positive control) on diastolic blood pressure (DBP) of SHRs during 28 days of oral administration and compared to the control group (*: $P<0.05$; : $P<0.01$; *: $P<0.001$; Mean±S.E.M.; n=6).

The SBP, DBP, and MAP of the SHRs were measured during the 28 days of sub-chronic oral administration of different drugs at 0.24273 g/kg (small), 0.48546 g/kg (medium), and 0.97092 g/kg (high) dosages of F1-2-treated groups, untreated group, and propranolol-treated group, and results are presented in FIGS. 11A, 11B, and 11C, respectively. Apparently, the SBP of the 0.24273, 0.48546, and 0.97092 g/kg of F1-2, and propranolol-treated SHRs were significantly lowered on week 4 to 187.97±3.06, 182.1±1.95, 168.69±3.59, and 182.08±2.38 mmHg (P<0.001), respectively compared to the control (225.81±2.77 mmHg). The DBP of SHRs during the 28 days of treatments by 0.24273, 0.48546, and 0.97092 g/kg of F1-2, as well as propranolol were dramatically decreased to 146.19±5.02, 133.36±3.99, 121.86±4.58, and 139.69±3.15 mmHg (P<0.001), respectively compared to control (189.19±3.61 mmHg). The MAP of the 0.24273, 0.48546, and 0.97092 g/kg of F1-2 and propranolol-treated groups also reduced abundantly to 159.72±4.12, 149.31±2.94, 136.78±4.07, and 152.06±3.10 mmHg (P<0.001), respectively compared to control (200.97±3.22) as shown in FIG. 11C. The SBP, DBP, and MAP of the F1-2-treated SHRs groups were reduced in dose-dependent manner.

SUMMARY

In the in vitro isolated aortic ring assays, a composition comprising *Uncaria* spp., *Pueraria* spp., *Panax notoginseng*, and *Alisma orientale* can induce up to is 101.71±3.64% of maximum relaxation ($R_{max}$) value in the phenylephrine (PE)-primed pre-contracted aortic rings at final concentration of 0.3175 mg/ml, with $EC_{50}$ value of 0.028±0.005 mg/ml. The signaling mechanism pathways employed by the composition to induce vasodilatory effects was mainly mediated by nitric oxide (NO)/soluble guanylyl cyclase (sGC)/cyclic guanosine monophosphate (cGMP) pathways, followed by prostacyclin ($PGI_2$), $β_2$-adrenergic, and muscarinic receptors pathways. Furthermore, the composition can regulate the vascular tone by controlling the membrane potential of the vascular smooth muscle cells via calcium-activated ($K_{ca}$), voltage-operated ($K_v$), ATP-sensitive ($K_{ATP}$), and inwardly-rectifying ($K_{ir}$) potassium channels. By acting as the potassium channels opener, the composition can enhance the hyperpolarizing current by allowing the potassium efflux. Most importantly, composition can act as calcium channels blocker for both voltage-operated calcium channels (VOCC) and inositol triphosphate receptor ($IP_3R$) to decrease the depolarizing current in vascular smooth muscle cells by inhibiting the calcium influx into the cytosol, hence reduce the formation of calcium-calmodulin complexes, and therefore causing vasodilatory effects.

In Vivo Antihypertensive Test of *Uncaria* spp., *Pueraria* spp., *Panax Notoginseng*, and *Alisma Orientale* Composition In the in vivo test, systolic blood pressure, diastolic blood pressure and mean arterial pressure (MAP) of spontaneous hypertensive rats (SHRs) were observed after 28 consecutive days of orally administration of a composition comprising *Uncaria* spp., *Pueraria* spp., *Panax notoginseng*, and *Alisma orientale* (F1-2) in three animal dosages (0.24273, 0.48546, and 0.97092 g/kg) together with propranolol as a positive control. The significances of the treated groups were compared to negative control (without treatment). All data expressed in mean±S.E.M.

The BP values of the composition-treated SHRs were significantly decreased to the values as expected. According to the results shown, there was up to 25/35% of systolic/diastolic blood pressure reduced within 28 days consecutive oral administration of the composition in SHRs. Additionally, the anti-hypertensive effects of the composition was inferred as dose-dependence manner, and was reliable in the use for treating hypertension disease.

INDUSTRIAL APPLICATION

The present invention is industrially applicable. The vasodilatory effect exhibited by the herb combination as described is extremely useful for antihypertensive drug development.

While in the foregoing specification this invention has been described in relation to certain preferred exemplary embodiments thereof and many details have been set forth for purpose of illustration, it will be apparent to those skilled in the art that the invention is susceptible to additional embodiments and that certain of the details described herein can be varied considerably without departing from the basic principles of the invention.

The invention claimed is:

1. A method for obtaining a composition for treating hypertension and hypertension-related complications, the method comprising:
   i. drying *Uncaria rhynchophylla, Pueraria thomsonii, Panax notoginseng*, and *Alisma orientale*;
   ii. grinding the dried *Uncaria rhynchophylla, Pueraria thomsonii, Panax notoginseng*, and *Alisma orientale* into powder;
   iii. mixing the ground dried *Uncaria rhynchophylla, Pueraria thomsonii, Panax notoginseng*, and *Alisma orientale* in a weight ratio ranging from 2.32-7.35:0.44-4.44:7.24-11.24:1-3, respectively, to form a mixture;
   iv. subjecting the mixture to an extraction method selected from the group consisting of maceration, liquid-liquid extraction, decoction, solid-phase extraction, solid-phase microextraction, Soxhlet extraction, and fizzy extraction; and
   v. separating an extract containing the composition from the mixture, wherein the extraction method is carried out at 50° C. and a solvent for the extraction method is ethanol.

2. The method according to claim 1, wherein the *Uncaria rhynchophylla, Pueraria thomsonii, Panax notoginseng*, and *Alisma orientale* are prepared in effective concentration of EC15-35, EC10-30, EC10-30, and $EC_{1-20}$, respectively.

3. The method according to claim 1, wherein the weight ratio of the ground dried *Uncaria rhynchophylla* to *Pueraria thomsonii* to *Panax notoginseng* to *Alisma orientale* is 5.32:2.44:9.24:1, respectively.

4. The method according to claim 1, wherein the extraction method is maceration.

5. The method according to claim 4, wherein a concentration of ethanol is 50%.

6. A composition for treating hypertension and hypertension-related complications, the composition obtained by a method comprising the steps of:
   i. drying *Uncaria rhynchophylla, Pueraria thomsonii, Panax notoginseng*, and *Alisma orientale*;
   ii. grinding the dried *Uncaria rhynchophylla, Pueraria thomsonii, Panax notoginseng*, and *Alisma orientale* into powder;
   iii. mixing the ground dried *Uncaria rhynchophylla, Pueraria thomsonii, Panax notoginseng*, and *Alisma orientale* in a weight ratio ranging from 2.32-7.35:0.44-4.44:7.24-11.24:1-3, respectively, to form a mixture;
   iv. subjecting the mixture to an extraction method selected from the group consisting of maceration, liquid-liquid extraction, decoction, solid-phase extraction, solid-phase microextraction, Soxhlet extraction, and fizzy extraction; and
   v. separating an extract containing the composition from the mixture, wherein the extraction method is carried out at 50° C. and a solvent for the extraction method is ethanol.

7. The composition according to claim 6, wherein the composition is free of any other herbs except for *Uncaria rhynchophylla, Pueraria thomsonii, Panax notoginseng*, and *Alisma orientale*.

* * * * *